US012629145B2

(12) United States Patent
Douglass et al.

(10) Patent No.: US 12,629,145 B2
(45) Date of Patent: May 19, 2026

(54) IMPLANT DEVICE, SYSTEM AND METHOD

(71) Applicant: AEVUMED, INC., Malvern, PA (US)

(72) Inventors: Robert P. Douglass, Bryn Mawr, PA (US); Miles O. Curtis, Philadelphia, PA (US); Saif Khalil, Malvern, PA (US); Paul M. Sethi, Malvern, PA (US); Nickolas G. Garbis, Malvern, PA (US); Michael C. Cusick, Malvern, PA (US); David L. Glaser, Malvern, PA (US)

(73) Assignee: AEVUMED, INC., Malvern, PA (US)

( * ) Notice: Subject to any disclaimer, the term of this patent is extended or adjusted under 35 U.S.C. 154(b) by 399 days.

(21) Appl. No.: 18/454,157

(22) Filed: Aug. 23, 2023

(65) Prior Publication Data

US 2024/0090889 A1     Mar. 21, 2024

Related U.S. Application Data

(60) Provisional application No. 63/488,631, filed on Mar. 6, 2023, provisional application No. 63/373,604, filed on Aug. 26, 2022.

(51) Int. Cl.
| | |
|---|---|
| *A61B 17/04* | (2006.01) |
| *A61B 17/00* | (2006.01) |
| *A61B 17/29* | (2006.01) |
| *A61B 90/00* | (2016.01) |

(52) U.S. Cl.
CPC .. *A61B 17/0401* (2013.01); *A61B 2017/0409* (2013.01); *A61B 2017/0464* (2013.01)

(58) Field of Classification Search
CPC ............ A61B 17/0401; A61B 17/0483; A61B 17/0485; A61B 17/06166; A61B 2017/0042; A61B 2017/0409; A61B 2017/0445; A61B 2017/0451; A61B 2017/0453; A61B 2017/0454; A61B 2017/0464; A61F 2/0805; A61F 2/0811
See application file for complete search history.

(56) References Cited

U.S. PATENT DOCUMENTS

| | | | | | |
|---|---|---|---|---|---|
| 2013/0197575 | A1* | 8/2013 | Karapetian | ........ | A61B 17/0401 606/232 |
| 2022/0323198 | A1* | 10/2022 | Zenz-Olson | ....... | A61B 17/0401 |

* cited by examiner

*Primary Examiner* — Tan-Uyen T Ho
*Assistant Examiner* — Lindsey R. Rivers
(74) *Attorney, Agent, or Firm* — Riverside Law LLP

(57) ABSTRACT

An implant system includes an implant having a body having a proximal end, a distal end, a central cavity disposed between the proximal and distal end, and a proximal end opening disposed proximal to the central cavity. A toggle is at least partially housed within the central cavity and connected to the body by a toggle hinge connection, the toggle having a toggle lumen extending therethrough. An inserter includes an inserter lumen, and an actuator having a distal actuator tip configured to advance into the proximal end opening. An implant system, kit, method for placing an implant device, devices and systems using a pivot suture, suture loading device and related surgical procedures are also disclosed.

31 Claims, 28 Drawing Sheets

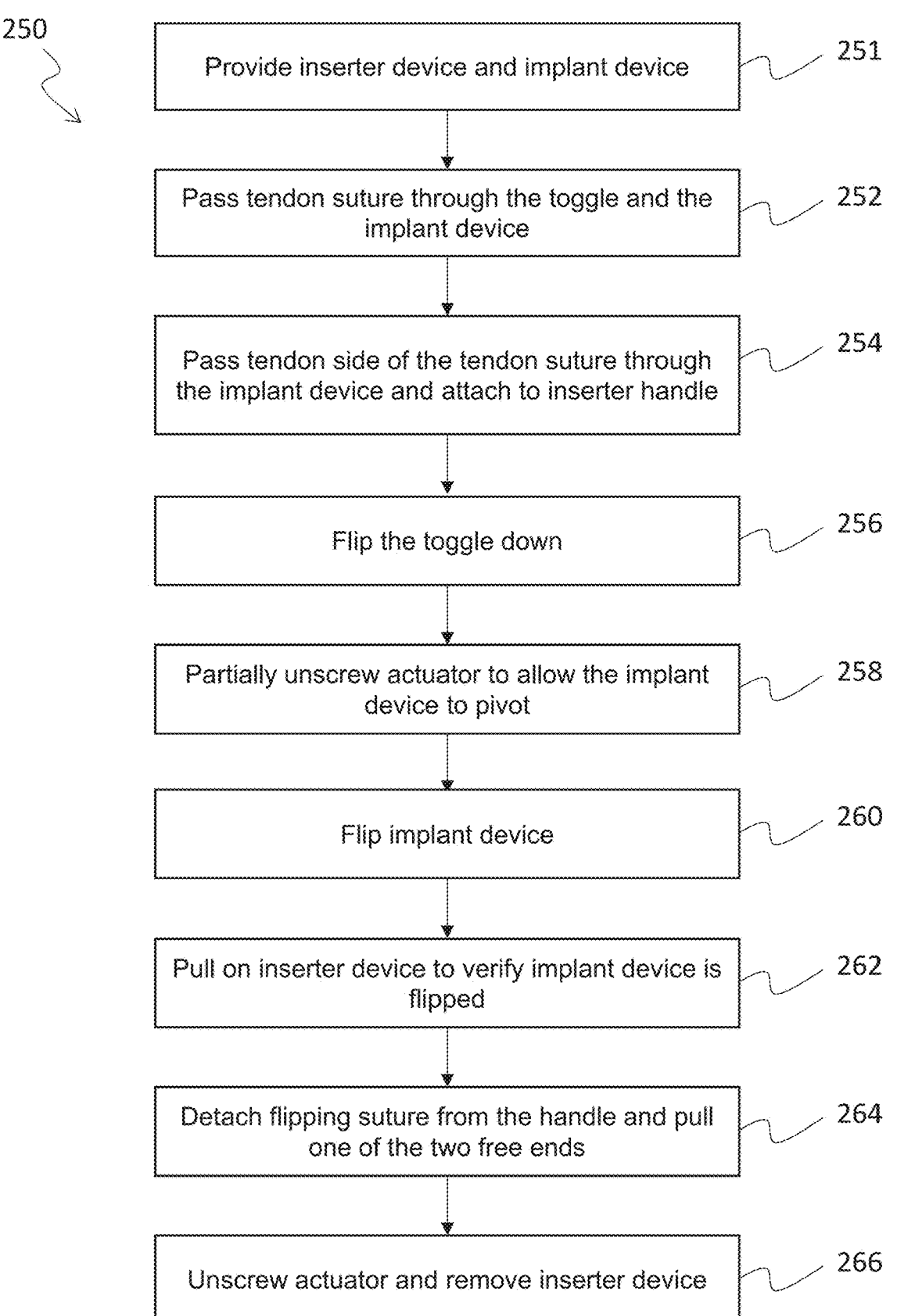

250

Provide inserter device and implant device — 251

Pass tendon suture through the toggle and the implant device — 252

Pass tendon side of the tendon suture through the implant device and attach to inserter handle — 254

Flip the toggle down — 256

Partially unscrew actuator to allow the implant device to pivot — 258

Flip implant device — 260

Pull on inserter device to verify implant device is flipped — 262

Detach flipping suture from the handle and pull one of the two free ends — 264

Unscrew actuator and remove inserter device — 266

FIG. 5

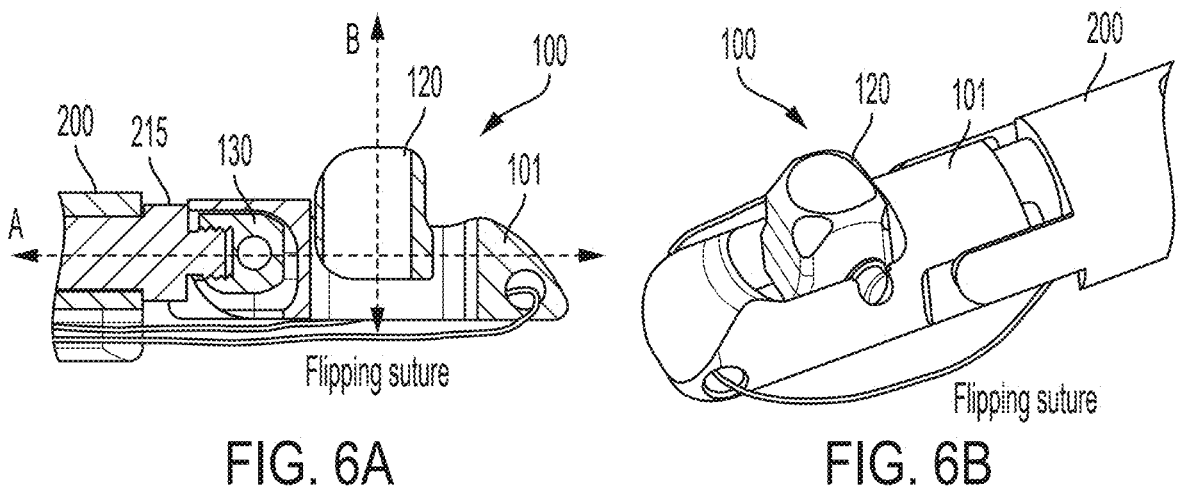
FIG. 6A                    FIG. 6B
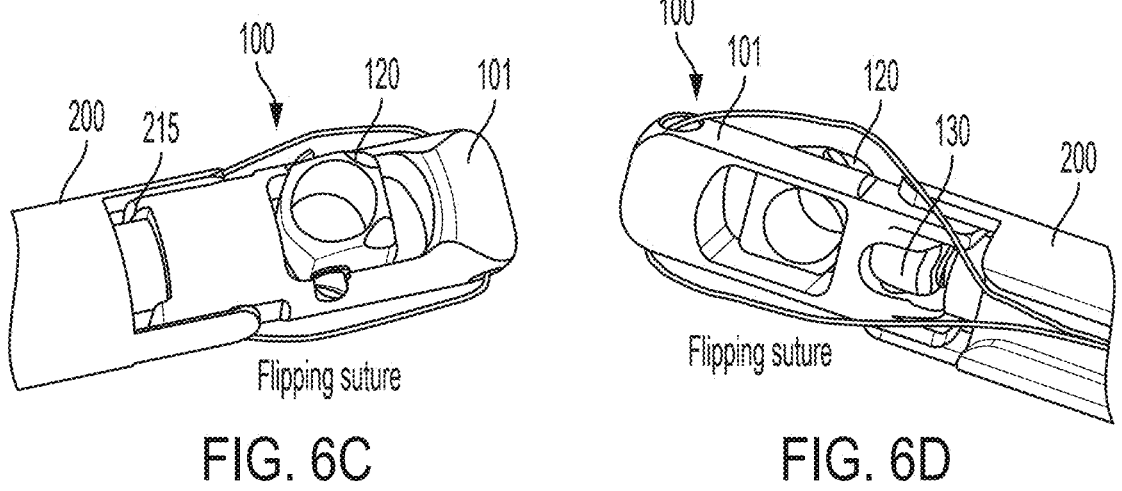
FIG. 6C                    FIG. 6D

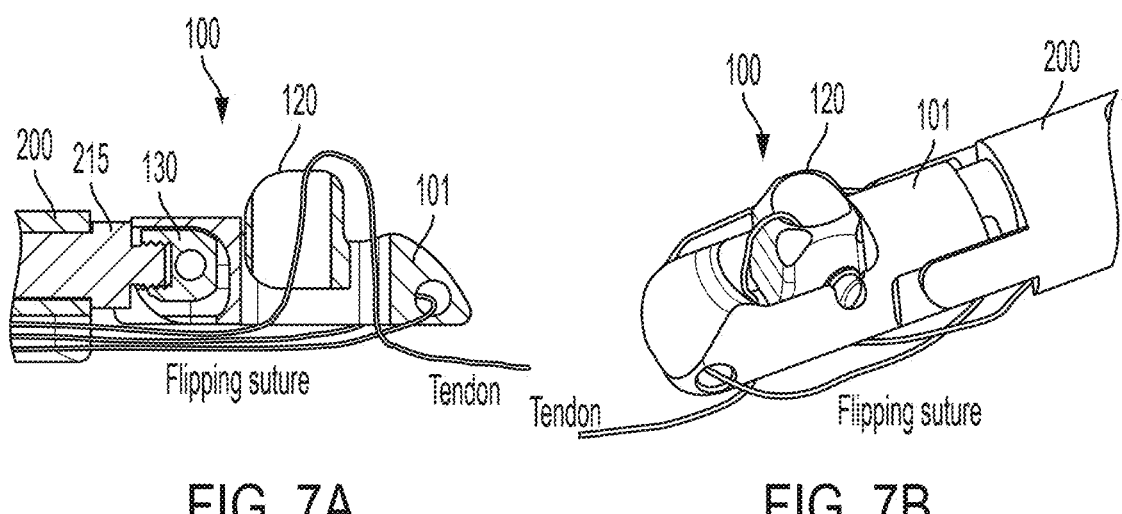
FIG. 7A                              FIG. 7B
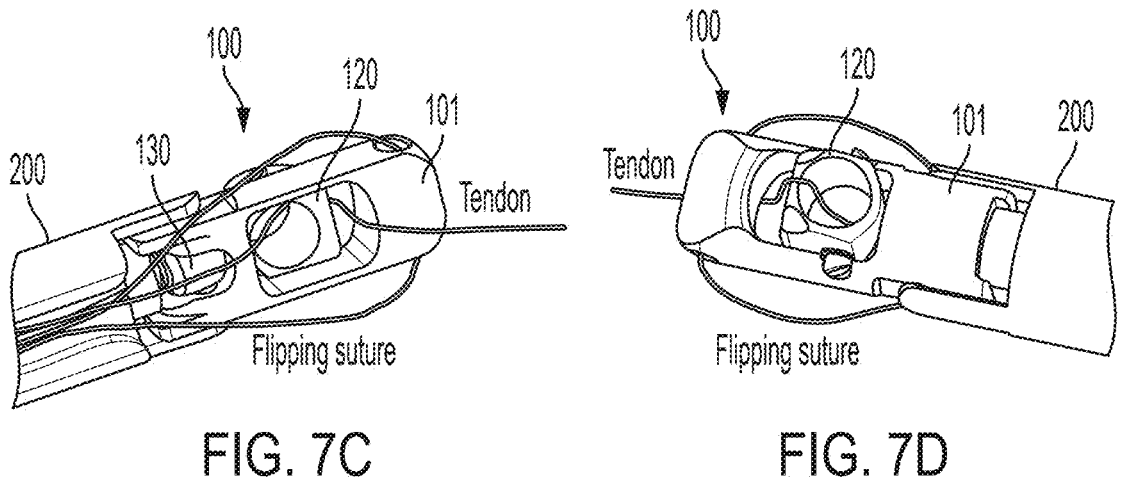
FIG. 7C                              FIG. 7D

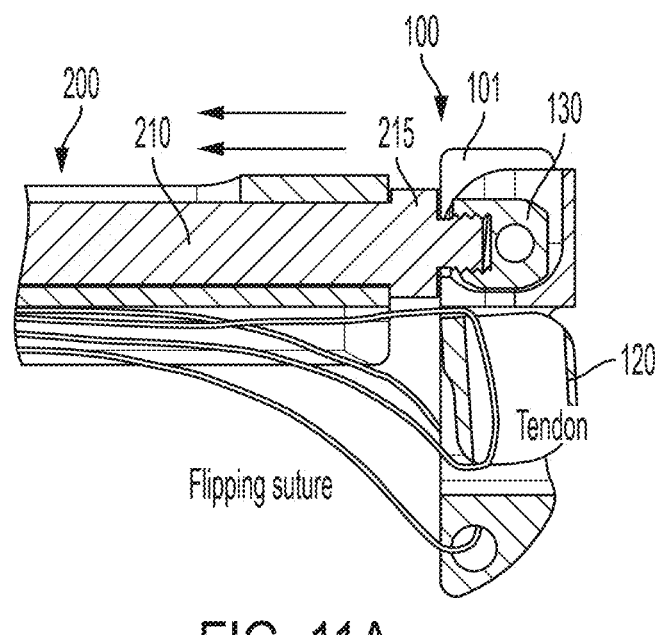
FIG. 11A
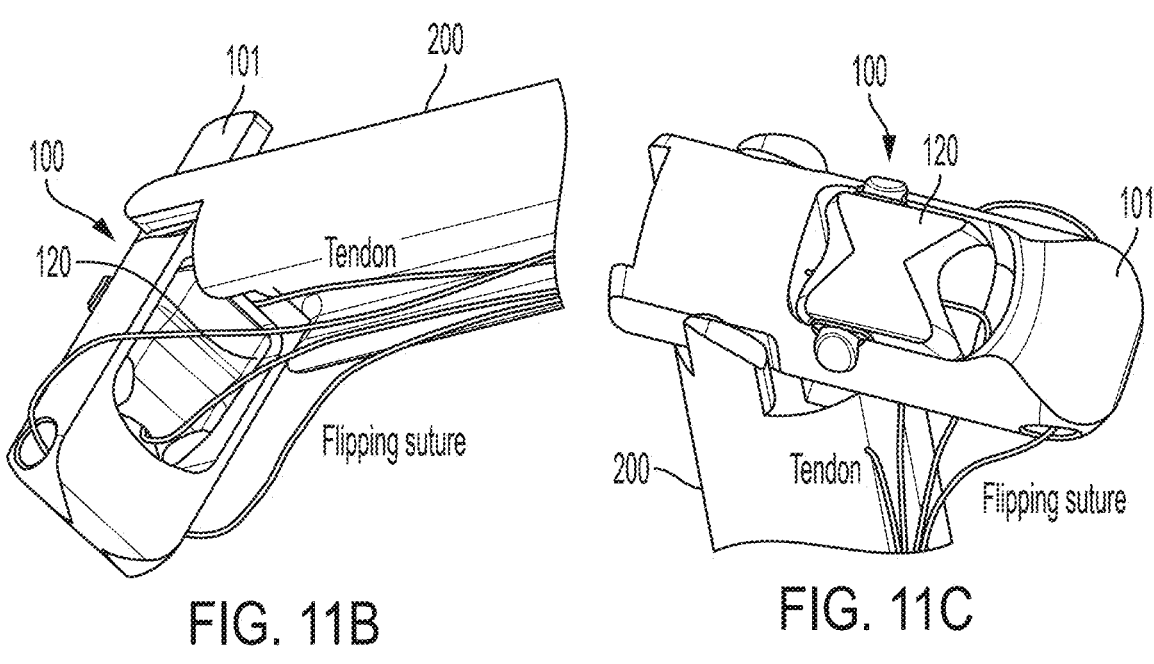
FIG. 11B          FIG. 11C

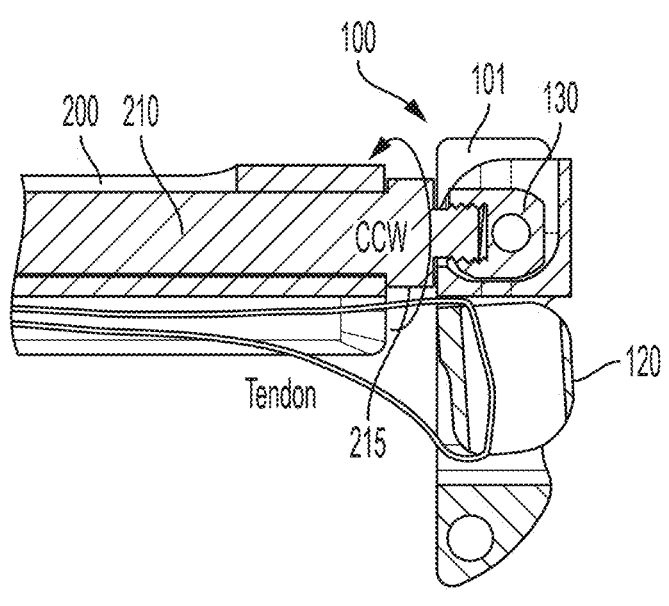
FIG. 13A
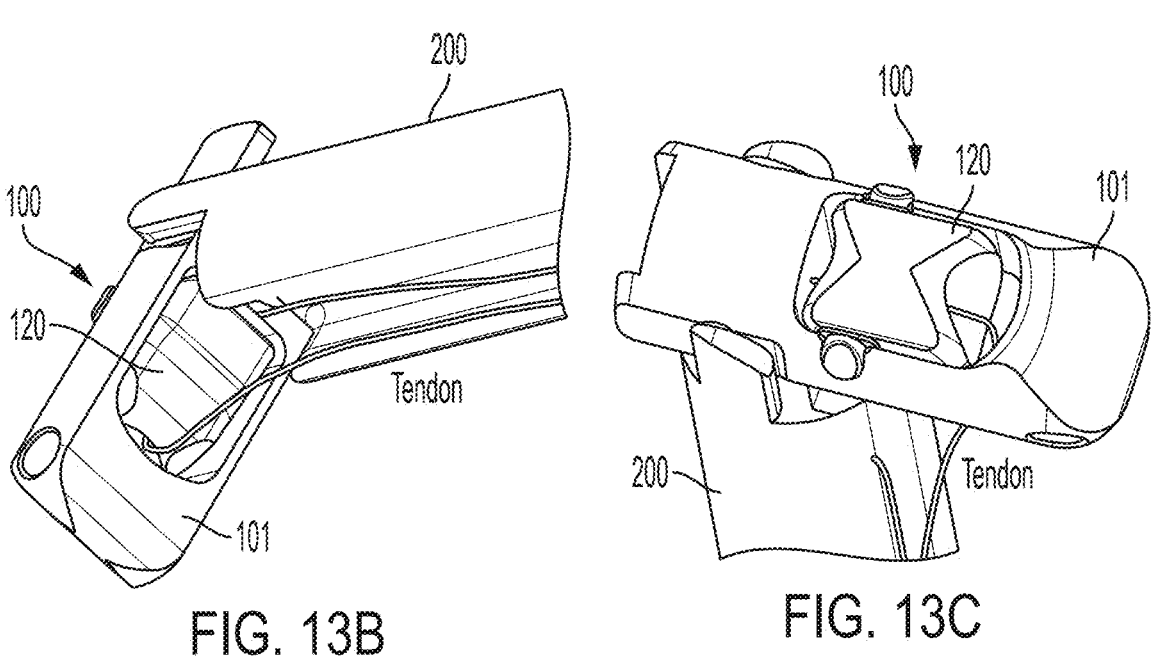
FIG. 13B                    FIG. 13C

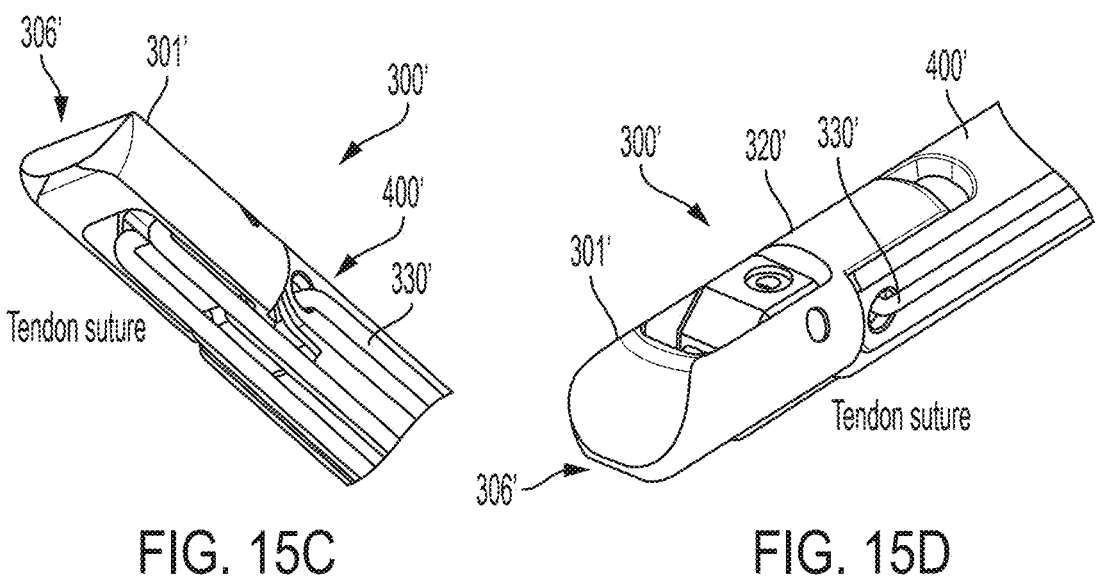
FIG. 15C
FIG. 15D
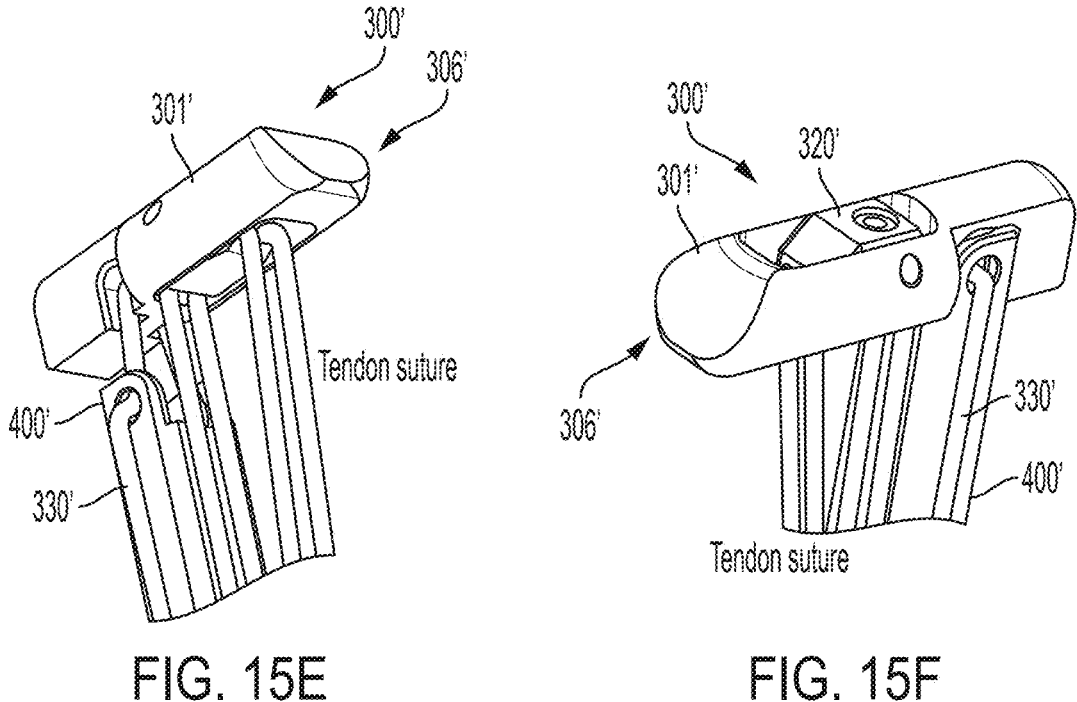
FIG. 15E
FIG. 15F

Figure 18A:
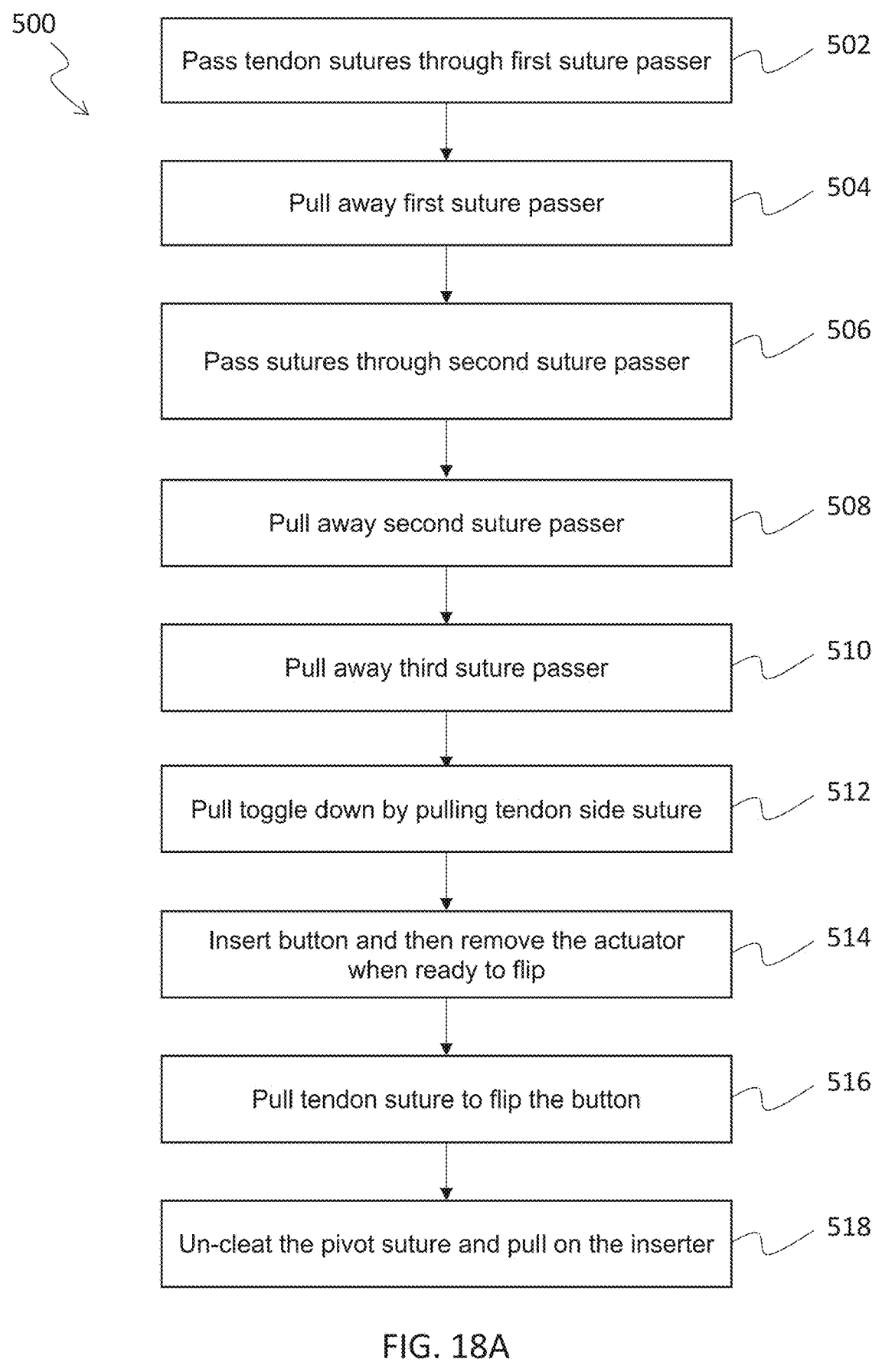

500

| |
|---|
| Pass tendon sutures through first suture passer | 502 |
| Pull away first suture passer | 504 |
| Pass sutures through second suture passer | 506 |
| Pull away second suture passer | 508 |
| Pull away third suture passer | 510 |
| Pull toggle down by pulling tendon side suture | 512 |
| Insert button and then remove the actuator when ready to flip | 514 |
| Pull tendon suture to flip the button | 516 |
| Un-cleat the pivot suture and pull on the inserter | 518 |

Step 1: Pass tendon sutures through first suture passer

504

Step 2: Pull away first suture passer

506

Step 3: Pass sutures through second suture passer

Step 4: Pull away second suture passer

Step 5: Pull away third suture passer

Step 6: Pull toggle down by pulling tendon side suture

Step 7: Insert button and then remove the actuator when ready to flip

514

516

Step 8: Pull on the flipping suture to flip the button (or pull tendon suture if flipping suture not being used)

Flipping suture

518

Step 9: Un-cleat the pivot suture and pull on the inserter

IMPLANT DEVICE, SYSTEM AND METHOD

CROSS-REFERENCE TO RELATED APPLICATIONS

This application claims priority to U.S. provisional application No. 63/373,604 filed Aug. 26, 2022, and U.S. provisional application No. 63/488,631 filed Mar. 6, 2023 both of which are incorporated herein by reference in their entireties.

BACKGROUND OF THE INVENTION

Surgical procedures such as a biceps tenodesis procedure are a common surgical treatment for biceps tendon tears and injuries (e.g. biceps tendonitis) or tears in the labrum. Biceps tenodesis generally involves detaching the biceps tendon from the labrum and moving the tendon to the humerus. Implant devices such as cortical buttons are commonly used in these procedures, as they provide a fixation point for sutures opposite to where the tendon is attached to the bone cortex, increasing surface contact between tendon and bone to promote better healing. The cortical button is typically advanced through a bone tunnel and tensioned at the bone cortex opposite the cortex where the tendon is attached, pulling the tendon back against the bone surface and facilitating surface contact. Cortical buttons have various geometries and can be used with other fixation devices such as a tenodesis screw.

However, conventional cortical button devices and systems have certain drawbacks. Conventional cortical buttons typically have no tensioning mechanism. Certain conventional devices rely on a tensioning mechanisms using a suture sleeve that the sutures passes through which unreliably tries to keep the tension in place due to friction in the sleeve preventing the sutures from sliding through it. Unfortunately, the suture sleeve is bulky, does not prevent slip, and it is not ideal for the surgeon to have to attach to the sutures preloaded into the sleeve. Where tensioning mechanisms have been suggested, the tensioning mechanisms can be difficult to engage depending on the button orientation, and the button orientation cannot be easily manipulated after insertion though the bone tunnel. They can also require use of a specific suture since conventional tensioning mechanisms lock at the same position every time, thus providing a specific dimension suture without the ability to accommodate a variety of commonly used sutures. Conventional tensioning mechanisms are also large, can only be used for proximal biceps tenodesis and not distal, and are limited in how surgeons can attach to the tendon.

What is needed in the art is an improved implant device, system and method with a tensioning mechanism having a mechanism that allows device orientation to be easily manipulated during the procedure, such as after the device is advanced through the bone tunnel.

SUMMARY OF THE INVENTION

In one embodiment, an implant device includes a body having a proximal end, a distal end, a central cavity disposed between 9 the proximal and distal end, and a proximal cavity disposed proximal to the central cavity, a toggle at least partially housed within the central cavity and connected to the body by a toggle hinge connection, the toggle having a toggle lumen extending therethrough, and a trunnion at least partially housed within the proximal cavity and connected to the body by a trunnion hinge connection, the trunnion having a proximal trunnion opening. In one embodiment, the body comprises a distal tip lumen extending laterally through the body. In one embodiment, the distal end of the main body has a blunt tip. In one embodiment, the proximal cavity comprises a proximal and bottom facing portion. In one embodiment, the toggle hinge connection comprises a set of toggle protrusions disposed on an upper proximal portion of the toggle. In one embodiment, the body comprises a set of toggle hinge openings configured to mate with the set of toggle protrusions. In one embodiment, the body comprises a set of trunnion hinge openings configured to mate with the set of trunnion protrusions. In one embodiment, the proximal trunnion opening comprises a threaded inner surface. In one embodiment, the trunnion is configured to rotate 90 degrees within the proximal cavity. In one embodiment, the body is restricted to flipping between an insertion position and a 90-degree flipped position. In one embodiment, a proximal portion of the body is configured with a geometry accommodating a plurality of locked orientation angles. In one embodiment, the toggle is configured to exert a unidirectional locking force. In one embodiment, the unidirectional locking force corresponds to a distance between the toggle and an adjacent wall that can vary based suture size. In one embodiment, the distance decreases as the toggle closes. In one embodiment, an angle between the toggle and the adjacent wall changes as the toggle closes. In one embodiment, the toggle is configured to exert the unidirectional locking force at a plurality of distances from the adjacent wall.

In one embodiment, an implant system includes the implant device, and an inserter device having an elongate actuator having a proximal and distal end, the actuator having a proximal actuator control and a distal actuator connection tip configured to advance into the proximal trunnion opening, and an elongate inserter tube at least partially coaxially surrounding the actuator. In one embodiment, the actuator is rotatable within the inserter tube. In one embodiment, the distal actuator connection tip comprises a threaded tip. In one embodiment, the elongate inserter tube comprises at least one distal protrusion configured to interface with at least one proximal surface of the body. In one embodiment, the elongate inserter tube comprises a set of distal protrusions configured to interface with a set of proximal surfaces of the body. In one embodiment, interfaces between the set of distal protrusions and the set of proximal surfaces of the body are planar. In one embodiment, the set of proximal surfaces of the body are recessed into the body. In one embodiment, an outer surface profile of the system at the interface is substantially circular with a flat bottom portion. In one embodiment, an outer surface profile of the system at the toggle is substantially circular with a flat bottom portion. In one embodiment, an outer surface profile on the system at the interface and the toggle is substantially the same profile. In one embodiment, the distal actuator connection tip configured to mate with the proximal trunnion opening via a threaded connection. In one embodiment, the inserter device comprises an inserter handle at least partially disposed over at least a portion of the actuator. In one embodiment, the actuator extends through a proximal opening in the inserter handle. In one embodiment, the proximal actuator control is connected to the actuator proximal of the inserter handle. In one embodiment, the proximal control is a twist knob. In one embodiment, the inserter handle comprises a curved arm extending away from its proximal end. In one embodiment, the curved arm is flexible. In one embodiment, the inserter handle comprises a channel adjacent to the curved arm.

In one embodiment, a kit comprising the implant system includes a suture preloaded through a distal tip lumen extending laterally through the body.

In one embodiment, a method for placing an implant device includes the steps of providing the system, passing a tendon suture through the toggle and the implant device, passing the tendon side of the tendon suture through the implant device and attaching to inserter handle, flipping the toggle down, partially unscrewing the actuator to allow the implant device to pivot, flipping the implant device, pulling on the inserter device to verify implant device is flipped, and unscrewing the actuator and removing the inserter device.

In one embodiment, a biceps tenodesis surgical procedure includes the method. In one embodiment, a shoulder, elbow, hand, wrist, knee, foot, ankle or hip surgical procedure includes the method.

In one embodiment, an implant system includes an implant comprising: a body having a proximal end, a distal end, a central cavity disposed between the proximal and distal end, and a proximal end opening disposed proximal to the central cavity, and a toggle at least partially housed within the central cavity and connected to the body by a toggle hinge connection, the toggle having a toggle lumen extending therethrough; and an inserter comprising: an inserter lumen, and an actuator having a distal actuator tip configured to advance into the proximal end opening. In one embodiment, both the distal actuator tip and the proximal end opening are threaded. In one embodiment, a proximal end of the actuator comprises a knob. In one embodiment, a distal end of the inserter comprises at least one arm. In one embodiment, the at least one arm comprises a first arm opening. In one embodiment, the first and second arm opening align with a pivot suture opening in the body. In one embodiment, the body is restricted to flipping between an insertion position and a 90-degree flipped position. In one embodiment, a proximal portion of the body is configured with a geometry accommodating a plurality of locked orientation angles. In one embodiment, the toggle is configured to exert a unidirectional locking force. In one embodiment, the unidirectional locking force corresponds to a distance between the toggle and an adjacent wall that can vary based suture size. In one embodiment, the distance decreases as the toggle closes. In one embodiment, an angle between the toggle and the adjacent wall changes as the toggle closes. In one embodiment, the toggle is configured to exert the unidirectional locking force at a plurality of distances from the adjacent wall. In one embodiment, the body comprises a distal tip lumen extending laterally through the body. In one embodiment, the distal end of the main body has a blunt tip. In one embodiment, the toggle hinge connection comprises a set of toggle protrusions disposed on an upper proximal portion of the toggle. In one embodiment, the body comprises a set of toggle hinge openings configured to mate with the set of toggle protrusions. In one embodiment, the inserter comprises a set of distal protrusions configured to interface with a set of proximal surfaces of the body. In one embodiment, interfaces between the set of distal protrusions and the set of proximal surfaces of the body are planar. In one embodiment, the set of proximal surfaces of the body are recessed into the body. In one embodiment, an outer surface profile of the system at the interface is substantially circular with a flat bottom portion. In one embodiment, an outer surface profile of the system at the toggle is substantially circular with a flat bottom portion. In one embodiment, an outer surface profile on the system at the interface and the toggle is substantially the same profile. In one embodiment, the actuator extends through a proximal opening in an inserter handle. In one embodiment, a proximal actuator control is connected to the actuator proximal of the inserter handle. In one embodiment, the proximal control is a twist knob. In one embodiment, the inserter handle comprises a curved arm extending away from its proximal end. In one embodiment, the curved arm is flexible. In one embodiment, the inserter handle comprises a channel adjacent to the curved arm.

In one embodiment, a kit comprises the implant system and a suture preloaded through a distal tip lumen extending laterally through the body. In one embodiment, a kit comprises the implant system and a preloaded pivot suture.

In one embodiment, a method for placing an implant device includes the steps of providing the system; passing a tendon suture through the toggle and the implant device; passing the tendon side of the tendon suture through the implant device and attaching to inserter handle; flipping the toggle down; unscrewing the actuator to allow the implant device to pivot; flipping the implant device; pulling on the inserter device to verify implant device is flipped; and unscrewing the actuator and removing the inserter device. In one embodiment, a biceps tenodesis surgical procedure comprising the method. In one embodiment, a shoulder, elbow, hand, wrist, knee, foot, ankle or hip surgical procedure comprising the method.

In one embodiment, a suture loading device includes an internal loop tab having an internal loop recessed into a top surface, and a wire loop tab configured to connect to the internal loop tab, wherein the wire loop tab includes a wire loaded within the internal loop. In one embodiment, the wire is configured to pull though the internal loop as the wire loop tab is separated from the internal loop tab. In one embodiment, the wire has a looped portion. In one embodiment, an implant system includes the suture loading device preloaded onto an implant device, the implant device including a body having a proximal end, a distal end, a central cavity disposed between the proximal and distal end, and a proximal end opening disposed proximal to the central cavity, and a toggle at least partially housed within the central cavity and connected to the body by a toggle hinge connection, the toggle having a toggle lumen extending therethrough, wherein the wire is loaded within the toggle lumen and the central cavity.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 5 is a flow chart of a method for placing a tenodesis implant device according to one embodiment.

FIGS. 6A-6D are alternate perspective views of a tenodesis implant system according to one embodiment, illustrating an example embodiment of method step 251.

FIGS. 7A-7D are alternate perspective views of a tenodesis implant system according to one embodiment, illustrating an example embodiment of method step 252.

FIGS. 11A-11C are alternate perspective views of a tenodesis implant system according to one embodiment, illustrating an example embodiment of method step 260.

FIGS. 13A-13C are alternate perspective views of a tenodesis implant system according to one embodiment, illustrating an example embodiment of method step 264.

FIGS. 15C and 15D are alternate perspective functional views of an implant system without a separate flipping suture in a straight position according to one embodiment, and FIGS. 15E and 15F are alternate perspective functional views of an implant system without a separate flipping suture in a flipped position according to one embodiment.

FIGS. 18A-18J show a method for placing an implant device according to one embodiment.

DETAILED DESCRIPTION OF THE INVENTION

Figure 1A:
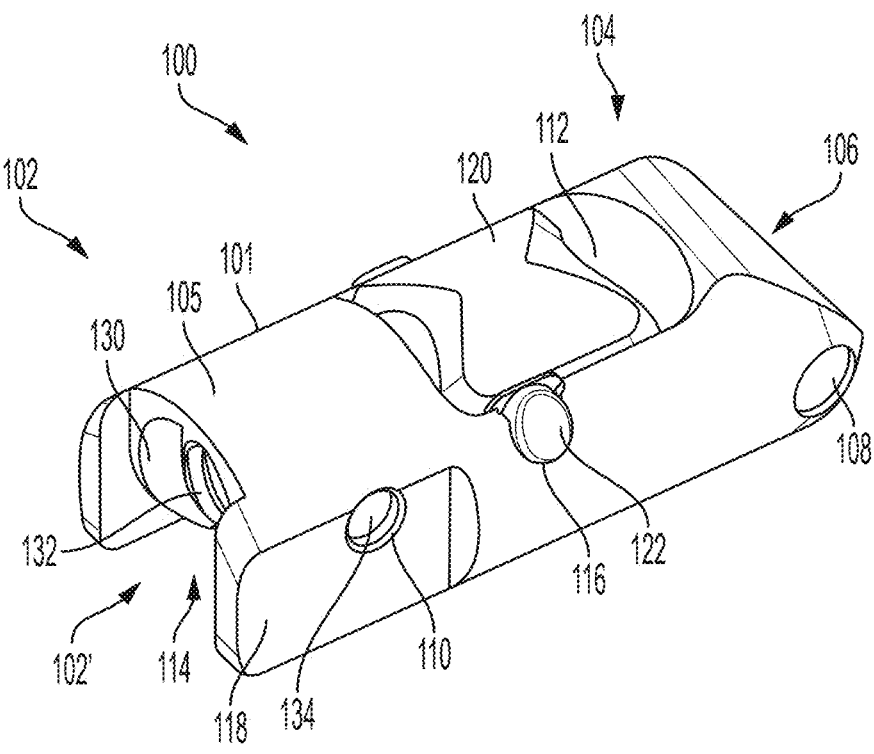
FIGS. 1A and 1B are top and bottom perspective views of a tenodesis implant device according to one embodiment.

It is to be understood that the figures and descriptions of the present invention have been simplified to illustrate elements that are relevant for a more clear comprehension of the present invention, while eliminating, for the purpose of clarity, many other elements found in implant devices, systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an implant device, system and method.

Embodiments of the device, system and method described herein have several advantages. For example, the self-cinching unidirectional tensioning mechanism utilizes a leverage mechanism that pinches the sutures in one direction only. It allows tendon tension to be tightened unidirectionally by pulling on the free suture end. The other end of the suture is locked and attached to tendon. The more force applied in disallowed direction, the more force that is leveraged into pinching the suture. The implant flipping mechanism implements mechanics that guarantees the implant will flip after advancement through the bone tunnel. This allows the surgeon to control when they release implant from its insertion position allowing it to rotate, and when they disengage from the button. Surgeons can now remain engaged with the implant even after the implant has fully flipped into position. Surgeons can pull on the inserter to feel and make sure that the implant has properly flipped into position and won't come out. They can lock and unlock button angle at any time using the actuator. Unscrewing the actuator allows the button to slightly pivot while pulling on the flipping sutures and the tendon side of the sutures passed through the button, which flips the button 90 degrees into its proper position. Note that as described herein, the tendon suture can flip the button in embodiments that do not utilize a flipping suture. Additional advantages are described in further detail below.

Figure 1B:
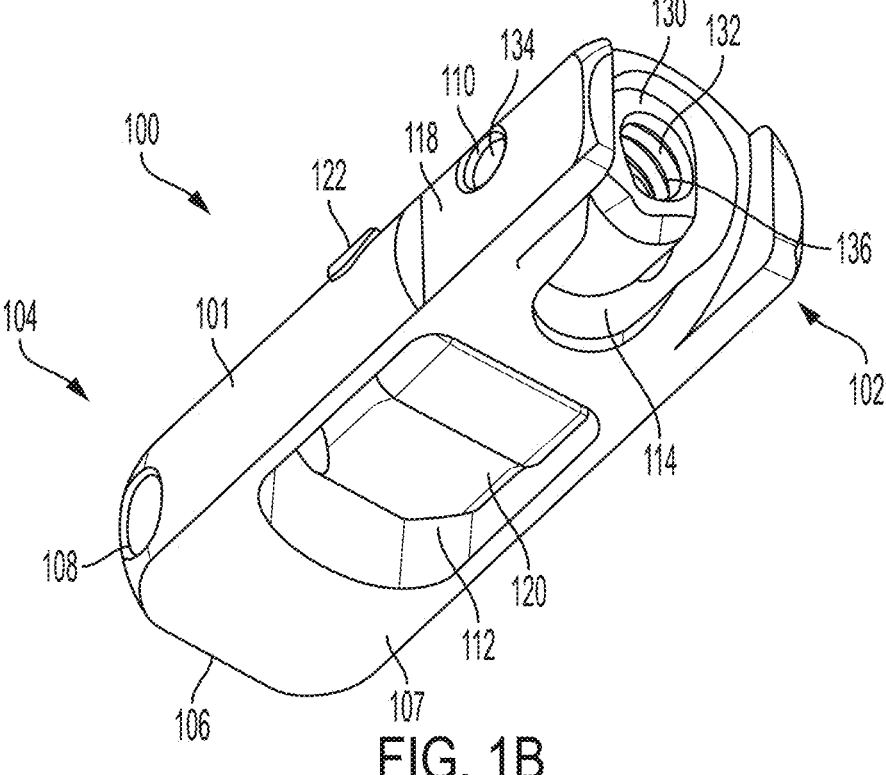
Figures 2A, 2B, 2C, 2D, 2E:
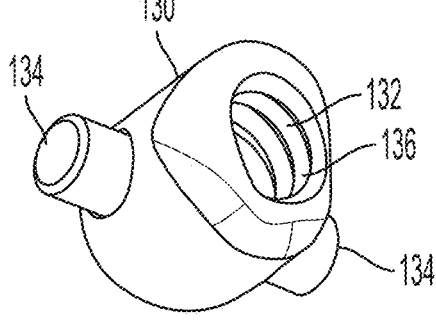
FIGS. 2A and 2B are top and bottom perspective views of an isolated body component according to one embodiment.
FIGS. 2C and 2D are top and bottom perspective views of an isolated toggle component according to one embodiment.
FIG. 2E is a perspective view of an isolated trunnion component according to one embodiment.

With reference now to FIGS. 1A and 1B, and isolated component views of FIGS. 2A-2E, a tenodesis implant device 100 is shown according to one embodiment. The tenodesis implant device 100 has a body 101 having a proximal end 102, a distal end 104 a top side 105 and a bottom side 107. A central cavity 112 disposed between the proximal end 102 and the distal end 104 for at least partially housing the toggle 120. A proximal cavity 114 is disposed proximal to the central cavity 112 for at least partially housing the trunnion 130. The central cavity 112 can for example open to the top and bottom of the tenodesis implant device 100. The proximal cavity 114 can for example include a bottom and proximal facing opening 102' such that the proximal cavity 114 at least partially defines a proximal and bottom facing opening in the body 101. The body 101 can include a distal tip lumen 108 extending laterally through the body 101. The geometry of the distal tip 106 of the body 101 is a blunt tip to facilitate advancement through patient anatomy. A set of proximal surfaces 118 can be recessed into the body 101 for interfacing with the inserter as explained in further detail below. The proximal surfaces 118 can be planar or substantially planar.

Figures 9A, 9B:
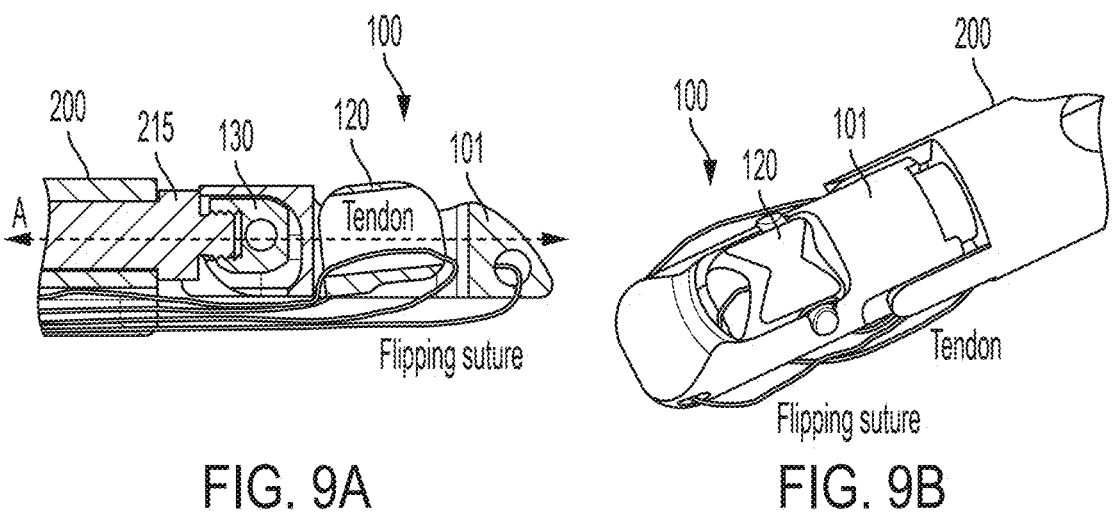
FIGS. 9A-9D are alternate perspective views of a tenodesis implant system according to one embodiment, illustrating an example embodiment of method step 256.
Figures 9C, 9D:
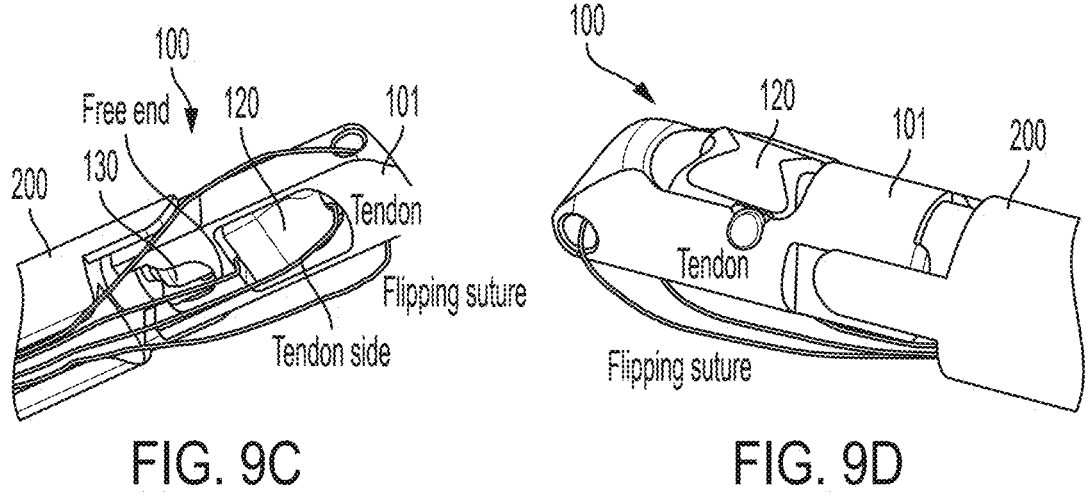
Figure 10A:
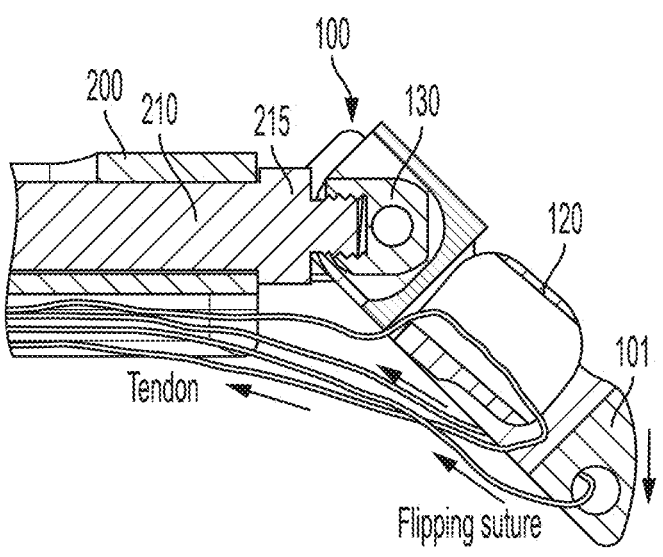
FIGS. 10A-10C are alternate perspective views of a tenodesis implant system according to one embodiment, illustrating an example embodiment of method step 258.
Figure 10B:
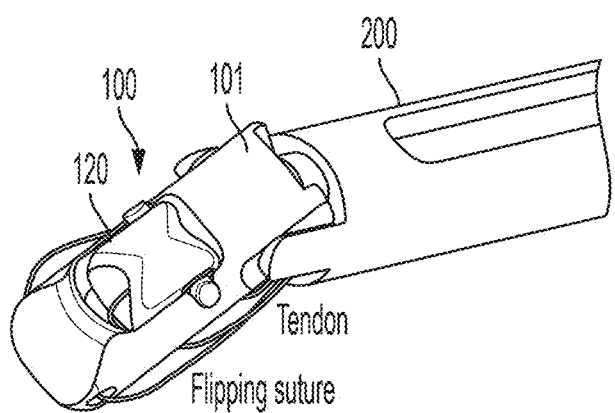
Figure 10C:
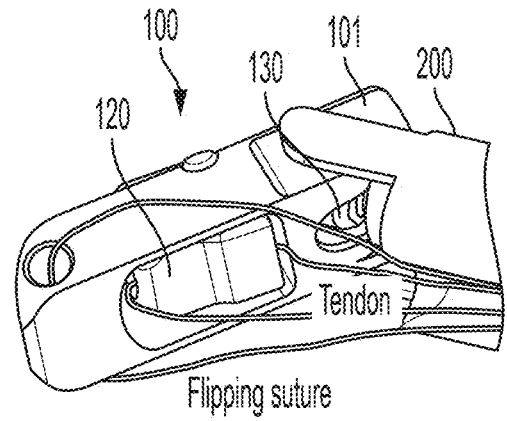
Figure 12A:
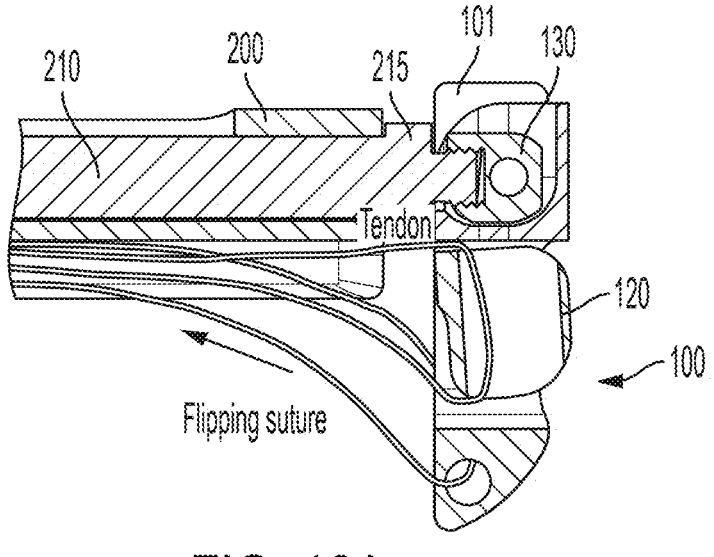
FIGS. 12A-12C are alternate perspective views of a tenodesis implant system according to one embodiment, illustrating an example embodiment of method step 262.
Figures 12B, 12C:
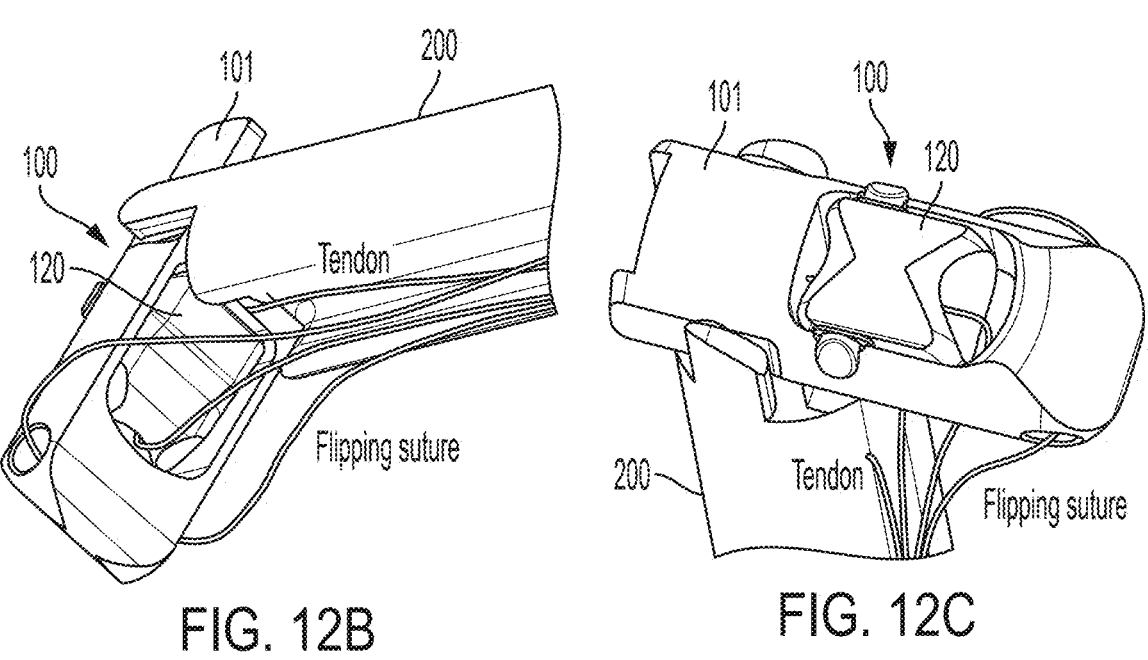

The toggle 120 has a toggle lumen 126 extending therethrough and is at least partially housed within the central cavity 112. The toggle 120 is connected to the body 101 by a toggle hinge connection. The toggle hinge is formed by a set of toggle protrusions 122 disposed on an upper proximal portion of the toggle 120. The body 101 includes a set of toggle hinge openings 116 configured to mate with the set of toggle protrusions 122, collectively forming the toggle hinge connection. In one embodiment, the toggle lumen 126 has a circular cross-sectional profile. The toggle lumen 126 can open (e.g. FIG. 6A) such that the longitudinal axis A of the implant device is substantially perpendicular to the longitudinal axis B of the toggle lumen 126. The toggle lumen 126 can close (e.g. FIG. 9A) such that the longitudinal axis A of the implant device is substantially parallel to or the same as the toggle lumen axis, or such that the toggle lumen 126 surrounds or is coaxial to the longitudinal axis A of the implant device 100. The toggle lumen can be various shapes, including for example substantially rectangular, oval or circular. In one embodiment, the toggle 120 forms a snap fit connection into the implant device 100. This way, it does not cut through much of the side of the body 101 and a separate pin is not required to form the hinge. The snap fit design allows the toggle to be formed as a single piece with integral hinge protrusions 122.

The trunnion 130 has a proximal trunnion opening 132 and is at least partially housed within the proximal cavity 114. The trunnion 130 is connected to the body 101 by a trunnion hinge connection. The trunnion hinge is formed by a set of trunnion protrusions 134 disposed on a distal portion of the trunnion 130. The body 101 includes a set of trunnion hinge openings 110 configured to mate with the set of trunnion protrusions 134. The proximal trunnion opening 132 includes a threaded inner surface 136. The geometry of the trunnion 130 and proximal cavity 114 interface to allow the body 101 to flip 90 degrees during the procedure. The body 101, toggle 120 and trunnion 130 can be made with one or more of a medical grade plastic or metal, including PEEK, Titanium, PEKK, Nitinol and PLGA. Similar to the toggle, the trunnion 130 can include a snap fit design that allows the trunnion to be formed as a single piece with integral hinge protrusions 134.

In one embodiment, the tenodesis implant device 100 is used as part of a system including the implant device 100 and an inserter device 200, shown in FIGS. 3A-3E according to one embodiment. The inserter device 200 has a proximal end 202 and distal end 204 and includes an elongate actuator 210. The actuator 210 has a proximal actuator control, which can for example be a twist knob 216. A distal actuator connection tip 212 is configured to fit and advance into the proximal trunnion opening 132. An elongate inserter tube 220 is at least partially coaxially loaded over the actuator 210. The actuator 210 is movable within the inserter tube 220, allowing for example a surgeon to rotate the actuator 210 while holding the inserter tube 220 stationary. The actuator 210 can rotate within the inserter tube 220 but cannot move axially. The inserter tube 220 can be connected to a handle 230 that can be sized for a comfortable ergonomic fit, including surface features such as recesses for a better grip and a curved arm 232 that can serve as a suture tie off point. The inserter tube 220 includes at least one distal protrusion configured to interface with at least one proximal surface of the body. In the embodiment depicted, a set of distal protrusions 222 are configured to interface with a set of proximal surfaces of the body 118. The interface 224 can be planar or substantially planar to prevent the implant device 100 from turning during actuation. Other non-planar interface geometries can be implemented to keep the implant device stationary during actuation as will be apparent to those having ordinary skill in the art. An outer or external surface profile of the system at the interface is substantially circular, facilitating smooth advancement though patent anatomy. Similarly, an outer surface profile of the system at the toggle can be substantially circular. Since an outer surface profile on the system at the interface and toggle is substantially the same, advancement of the system though patent anatomy becomes easier via the uniform external profile.

The distal actuator connection tip 212 is configured to mate with the proximal trunnion opening 136. In one embodiment, the connection is via a threaded connection, and the distal actuator connection tip 212 is threaded 214. The body 101 angle can be locked between 0 and 90 degrees by turning the actuator 210 to a locked position. In one embodiment, turning the actuator 210 clockwise loads the trunnion 130 onto the actuator connection tip 212, loading it further in a proximal direction as the actuator 210 turns. As the trunnion 130 moves proximally up the actuator, the actuator stop 215 begins to tightly interface with the adjacent portion of the body 101 (shown e.g. at FIG. 6A-13C) preventing body 101 movement about the trunnion hinge connection, allowing the trunnion 130 to lock the implant device 100 at a desired orientation.

Figures 3A, 3B, 3C, 3D, 3E:
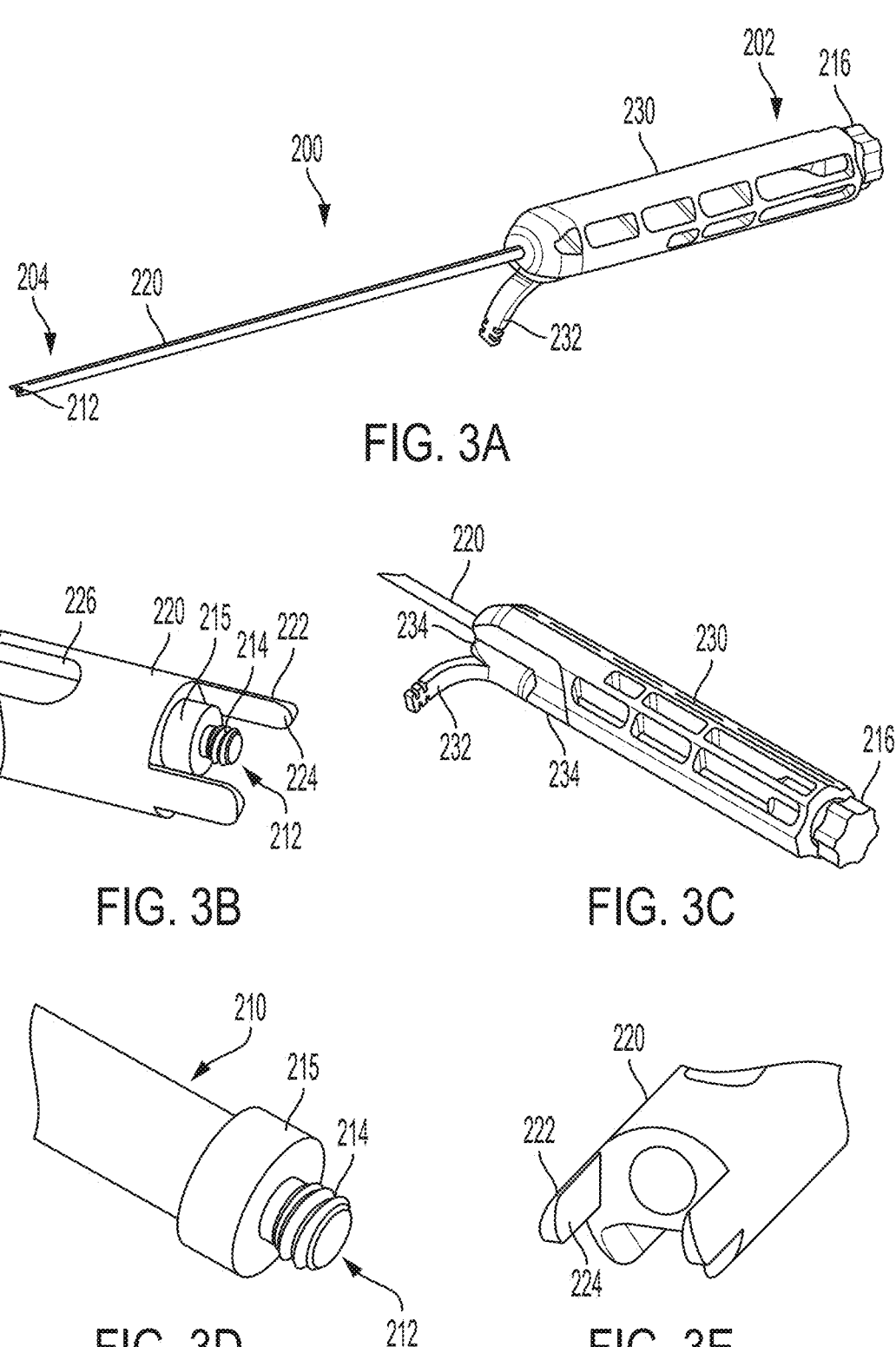
FIG. 3A is a perspective view of an inserter device according to one embodiment.
FIG. 3B is a magnified view of the inserter device tip.
FIG. 3C is a magnified view of the inserter device handle.
FIG. 3D is a magnified view of the actuator tip in isolation.
FIG. 3E is a magnified view of the inserter tube tip in isolation.
Figure 3F:
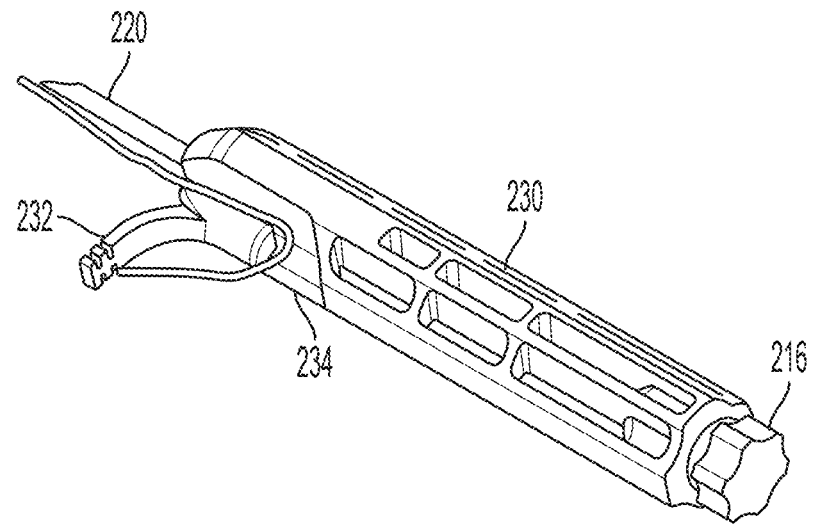
FIG. 3F is a partial perspective view of an inserter device handle showing a suture within the handle channel.

The inserter handle 230 is disposed coaxially over at least a portion of the actuator 210, and can extend through a proximal opening in the inserter handle 230. A proximal actuator control (e.g. a twist knob 216) is connected to the actuator 210 proximal of the inserter handle 230. A kit comprising including the tenodesis implant system and a suture preloaded through a distal tip lumen extending laterally through the body can be provided as referenced further below. Embodiments of the system come packaged with the flipping suture preloaded and tied to the inserter handle 230. The flipping suture can be tied to the curved arm 232. An adjacent channel 234 can be configured into the inserter handle 230 to guide the suture along the inserter tube 220 to the curved arm 232 (as shown for example in FIG. 3F). The surgeon can keep the sutures passed through the implant device 100, to the side and out of the way during implantation, or the sutures can be pulled along with the flipping sutures to better actuate the flipping of the implant device 100, or they can be tied to the curved 232 as well. The surgeon only needs to pull on flipping sutures to actuate a flip, but may also pull on the tendon side of the suture to help actuate if desired. Note that as described herein, the tendon suture can flip the button to eliminate the need for a flipping suture. In one embodiment the curved arm 232 can flex and flip the implant device without the surgeon pulling on the sutures. Accordingly, the curved arm 232 can flex and tension the suture enough to immediately flip the button as soon as the actuator is unscrewed. Flexing the curved arm 232 is optional, as the surgeon can instead pull on the sutures themselves.

Figure 4A:
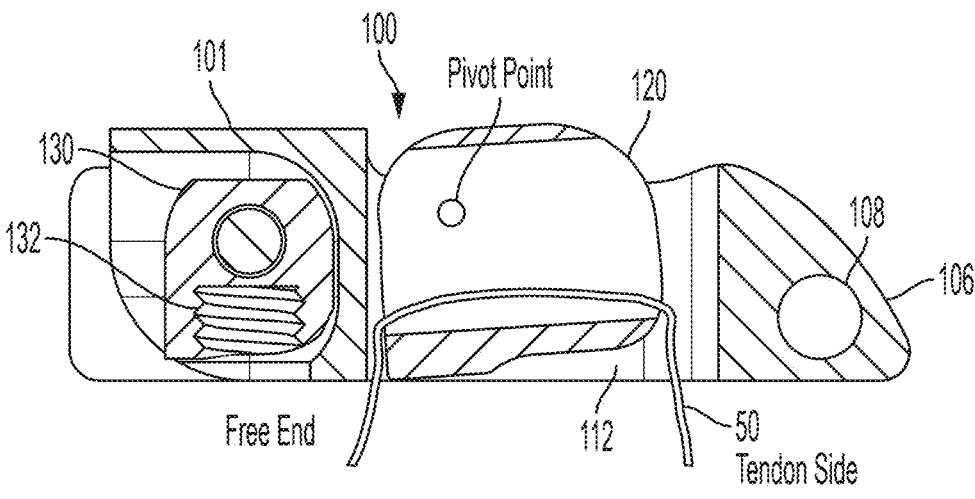
FIG. 4A is a side partial cutaway view of a tenodesis implant device according to one embodiment.
Figure 4B:
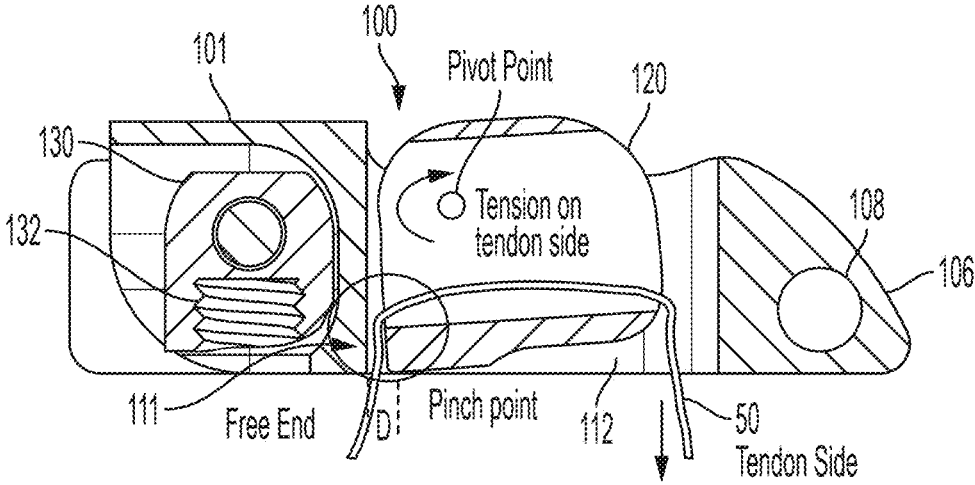
FIG. 4B illustrates the effect of tendon side tension on the toggle and suture.
Figure 4C:
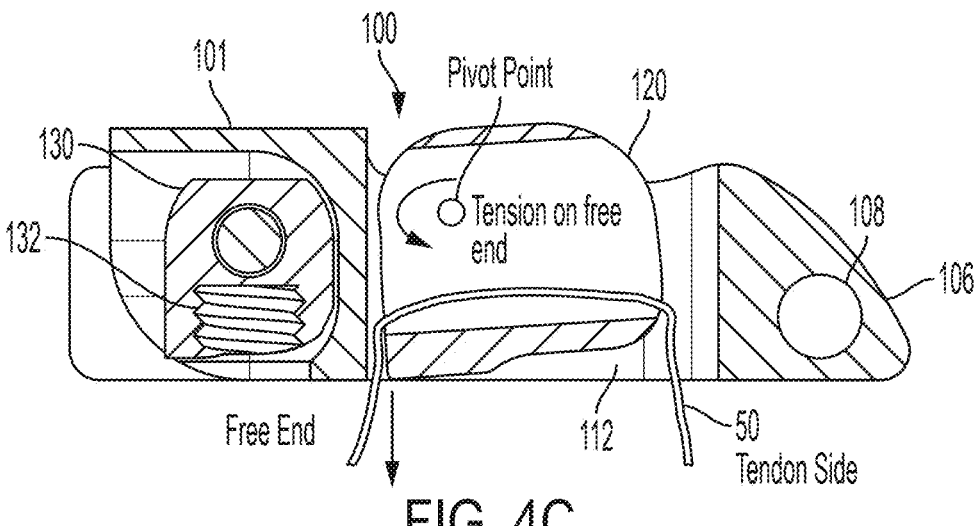
FIG. 4C illustrates the effect of free end tension on the toggle and suture.
Figure 8A:
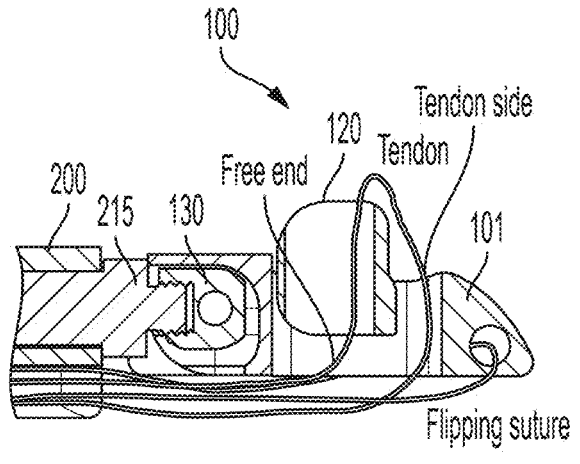
FIGS. 8A-8D are alternate perspective views of a tenodesis implant system according to one embodiment, illustrating an example embodiment of method step 254.
Figure 8B:
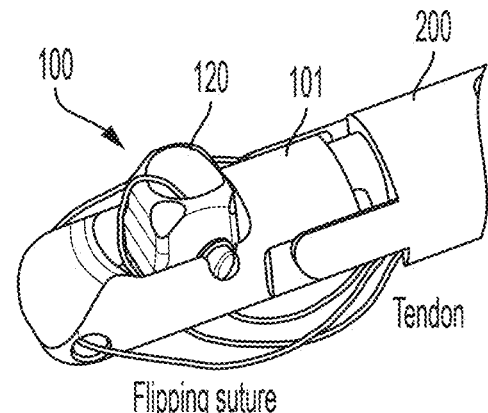
Figure 8C:
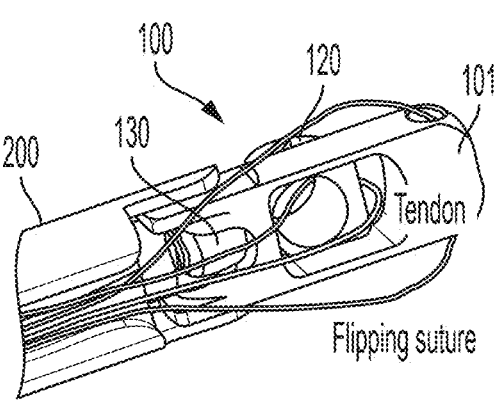
Figure 8D:
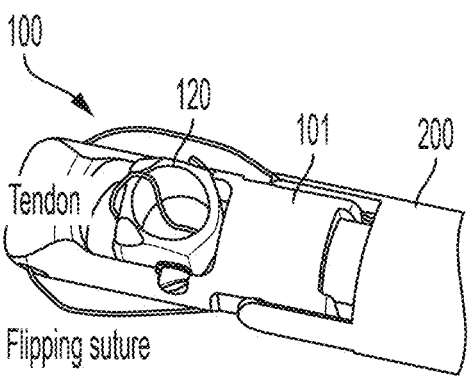

With reference now to FIGS. 4A-4C, the self-cinching tensioning mechanism is illustrated according to one embodiment. Pulling the free end of the suture 50 tightens the tendon tension and bring it closer to the implant 100. Leverage and pinch prevents the suture 50 from being pulled in the opposite direction. As illustrated specifically in FIG. 4B, tension on tendon side of suture 50 causes the toggle 120 to pivot clockwise and pinches the suture 50 between the toggle 120 and body 101 of the implant 100 as shown. The pinch point can be configured as two parallel walls for optimizing hold on the suture. As illustrated specifically in FIG. 4C, pulling on the free end of the suture 50 causes the toggle 120 to rotate counterclockwise, alleviating the pinch point. Accordingly, the toggle 120 allows the passage of sutures in one direction but disallows passage in the opposite direction. The toggle 120 pivots to utilize leverage in order to allow passage of sutures in one direction, then pinches and locks the sutures in the opposite direction. When the toggle 120 pivots to an open position, sutures can be pulled from the free end. When the toggle 120 pinches the sutures against the body 101, suture movement is arrested. Accordingly, the force pinching the sutures in the locked direction increases with the force pulling on the sutures in the locked direction. This allows the surgeon to pull the tendon to be the desired tension using the toggle mechanism without having to tie a knot. As the tendon will always keep tension on the locked side of the sutures, the tendon will always remain locked in its final position. Accordingly, while conventional tensioning mechanisms only work with a specific suture because the position at which it locks the suture is fixed and it locks at the same position every time, embodiments of the tensioning mechanism described herein can exert the unidirectional locking force at a plurality of distances from the adjacent wall. The distance between the toggle 120 and the adjacent wall 111 can vary depending on the size of the suture passed through (and thus the angle too), providing a device can work with a variety of sutures, not just one specifically. Thus, in one embodiment, the unidirectional locking force corresponds to a distance D between the toggle and an adjacent wall that varies based suture size. In one embodiment, the distance decreases as the toggle closes, and the angle between the toggle and the adjacent wall can also change as the toggle closes.

In addition, embodiments of the system allow the surgeon to check to make sure the implant is properly flipped and implanted by pulling on the inserter while the trunnion is still connected to the actuator. Since embodiments of the device feature sutures passed through the main body, the button can be easily flipped when the flipping sutures are pulled. If a separate flipping suture is utilized, it can be removed from the device after implantation by pulling on one of the two free ends. Note that as described herein, the tendon suture can flip the button so that a flipping suture is not required. Additionally, the locked end of the suture passed through the toggle can be pulled on to help actuate flipping of the implant. In one embodiment, the inserter handle features a thin arm meant for the sutures to be attached to that is capable of flexing to apply a constant pulling force on the flipping sutures to help actuate the flipping of the implant. Embodiments of the device can be used with tapes or sutures ranging from size #2 to #5. Embodiments of the device can be implanted into the bone unicortically or bicortically. Embodiments of the toggle can individually or simultaneously lock and unlock more than one suture passed through it at a time.

Figure 14A:
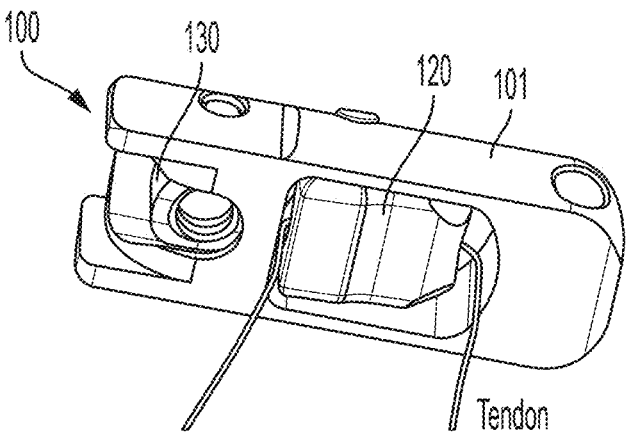
FIGS. 14A-14C are alternate perspective views of a tenodesis implant system according to one embodiment, illustrating an example embodiment of the placed tenodesis implant device.
Figure 14B:
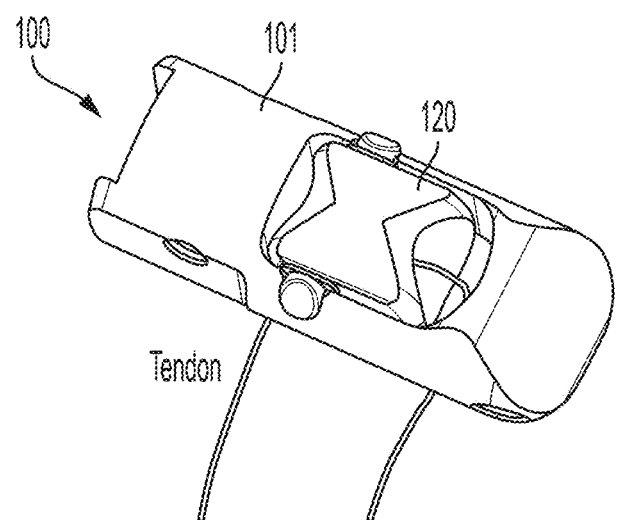
Figure 14C:
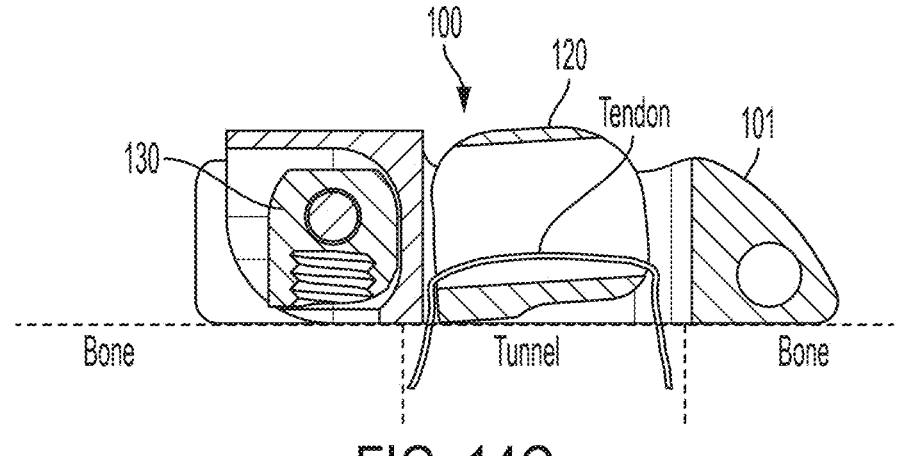

With reference now to FIG. 5, a method 250 of implanting the device is shown in the flow chart according to one embodiment. The method 250 includes the step of providing an inserter device 251. As shown for example in FIGS. 6A-6D, the implant device 100 can be provided pre-loaded onto inserter device 200 with the toggle 120 angled 90 degrees and with the flipping suture already tied to the handle and wrapped around through the front hole of the implant 100. Next, the tendon suture (or sutures) is passed through the toggle 120 and the implant device (100) 252. With reference for example in FIGS. 7A-7D, the tendon can be whipstitched per techniques known in the art, and the tendon sutures are passed through the toggle 120 and the implant device 100. Next, the tendon side of the tendon suture is passed through the implant device and attached to the inserter handle 254. As shown for example in FIGS. 8A-8D, the tendon side of the tendon suture is passed through the implant device and tied to the inserter handle. Next, the toggle if flipped down 256. As shown for example in FIGS. 9A-9D, the tendon suture is pulled on from the tendon side to flip the toggle 120 down and into place. The surgeon could also push the toggle to flip it down. Next, the actuator 210 is unscrewed slightly to allow the implant device 100 to pivot 258. As shown for example in FIGS. 10A-10C, unscrewing the actuator 210 allows the implant device 100 to pivot and the flipping suture (and tendon side of the tendon suture) can be pulled to actuate flipping. The actuator 210 can lock the implant device 100 at any angle by retightening the actuator 210. Next, the implant device 100 is flipped 260 via the flipping suture being pulled and/or the tendon side of the suture through the toggle (e.g. FIG. 10A). Next, the surgeon pulls on the inserter device 200 to verify the implant device is flipped 262. As shown for example in FIGS. 11A-11C, the implant device 100 is in the fully flipped position. The surgeon can now pull on the inserter device 200 to feel and verify that the implant device is indeed flipped. If the implant device is in proper position, it will not pull out of the bone tunnel when the surgeon pulls on the inserter. Next, the flipping suture is detached from the handle and one of the two free ends is pulled 264. As shown for example in FIGS. 12A-12C, to disengage from the implant device, the surgeon can untie the flipping suture from the handle and pull on one of the two free ends to remove the flipping suture completely. Note that as described herein, the tendon suture can flip the button so that a flipping suture is not required. Finally, the actuator 210 can be completely unscrewed and removed 266. As shown for example in FIGS. 13A-13C, to finish disengaging from the implant device, the surgeon can completely unscrew the actuator 210 (e.g. by twisting counter clockwise) to release the implant device 100, then pull the inserter device 200 away, removing the full inserter device assembly including the actuator and inserter tube from the surgical site. The result is the implant device advanced through the bone tunnel and properly positioned at the bone cortex opposite the cortex where the tendon is attached (see e.g. FIGS. 14A-14C).

Embodiments of the implant device, system and method can be implemented for several surgical procedures that require connecting tissue to bone, such as for example biceps tenodesis, ACL repair and reconstruction, MCL, PCL, LCL, and Achilles tendon repair. Surgical procedures on the shoulder may include for example Bankart lesion repair, SLAP lesion repairs acromio-clavicular repair, capsular shift/capsulolabral reconstruction, deltoid repair, rotator cuff tear repair, and biceps tenodesis treatment. Surgical procedures on the elbow may include for example ulnar or radial collateral ligament reconstruction, lateral epicondylitis repair, and bicep tendon reattachment. Surgical procedures on the hand and wrist may include for example collateral ligament repair, scapholunate ligament reconstruction, tendon transfers in phalanx, and volar plate reconstruction. Surgical procedures on the knee may include for example ACL/PCL repair and reconstruction, ACL/PCL patellar bone-tendon-bone grafts, double-tunnel ACL reconstruction, extracapsular repair MCL, LCL, and posterior oblique ligament, Illiotibial band tenodesis, patellar tendon repair, VMO advancement, and joint capsule closure. Surgical procedures on the toot and ankle may include for example medial/lateral repair and reconstruction, mid and forefoot repair, hallux valgus reconstruction, metatarsal ligament/tendon repair or reconstruction, Achilles tendon repair, and ankle syndesmosis fixation. Surgical procedures on the hip may include for example acetabular labral repair.

Figure 15A:
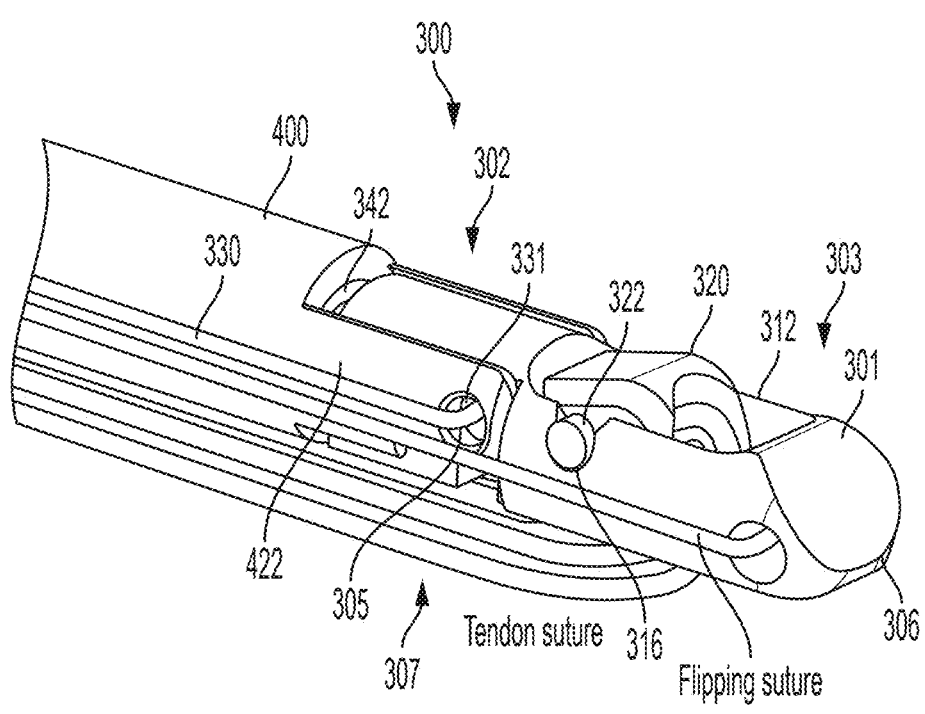
FIGS. 15A and 15B are perspective functional views of an implant system according to one embodiment in a straight position (FIG. 15A) and a flipped position (FIG. 15B)
Figure 15B:
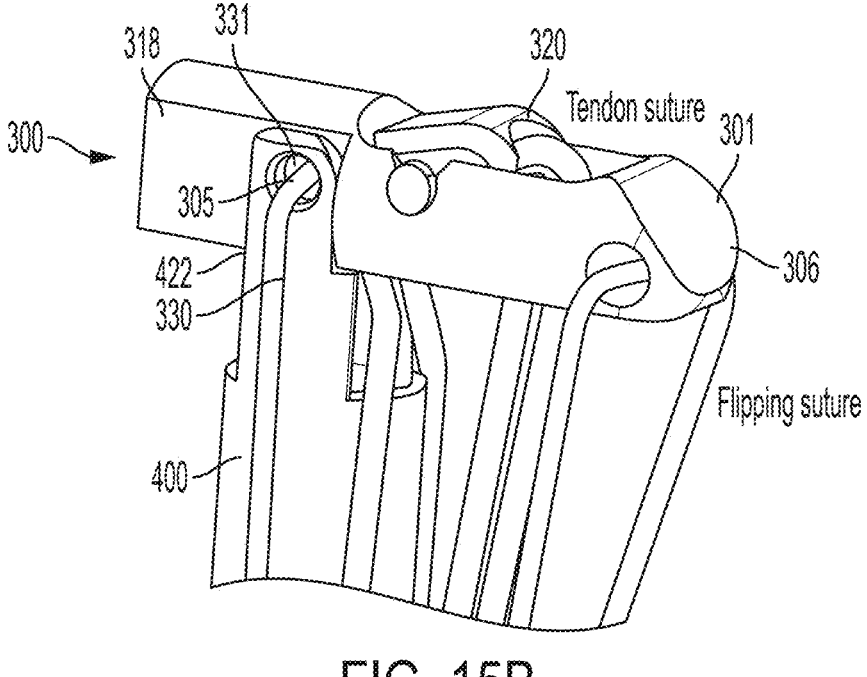
Figures 16A, 16B, 16C, 16D:
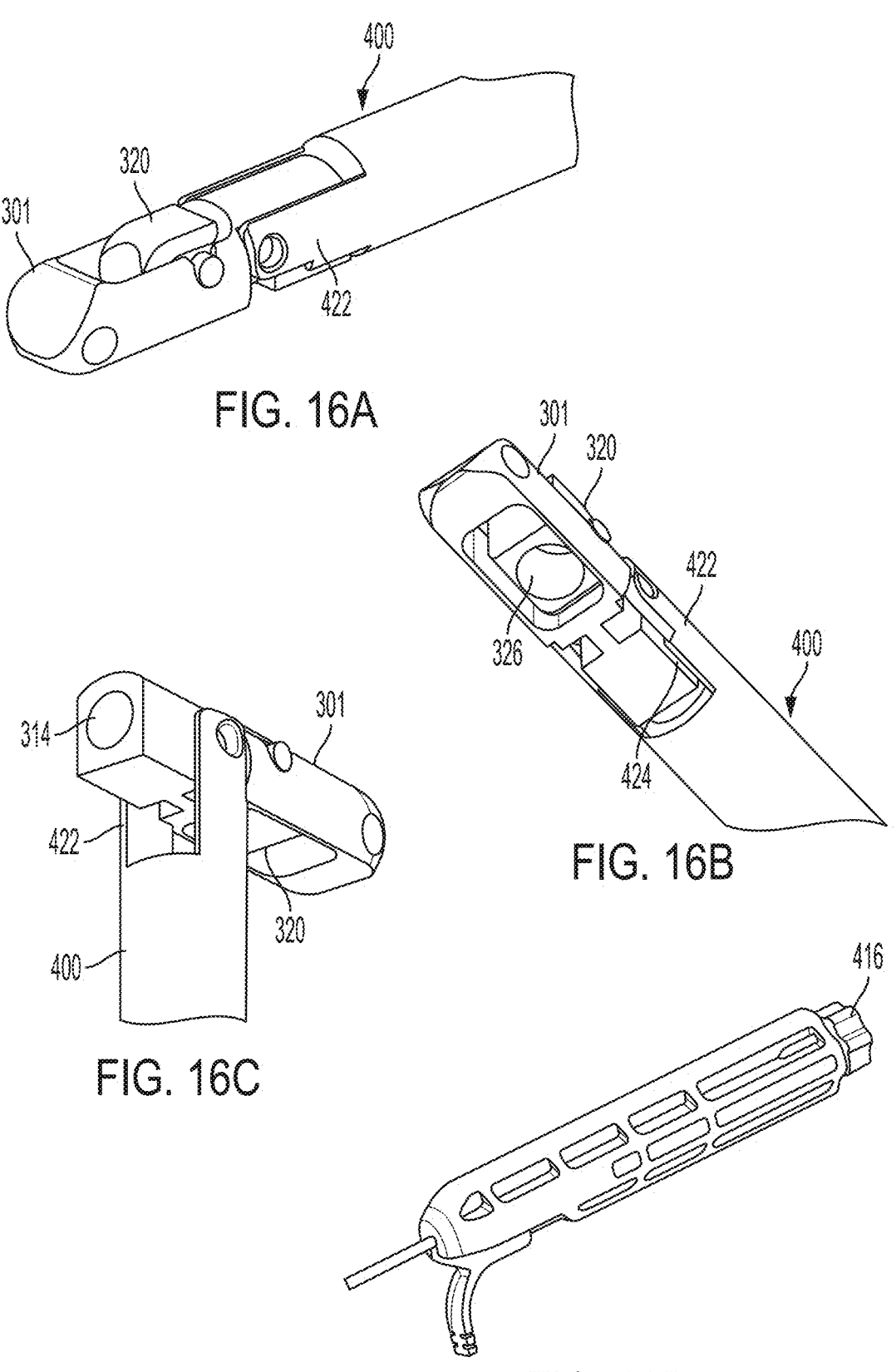
FIGS. 16A-16D are alternate partial perspective views of an implant system according to one embodiment in a straight position (FIGS. 16A and 16B), flipped position (FIG. 16C) and the handle region (FIG. 16D).
Figure 17A:
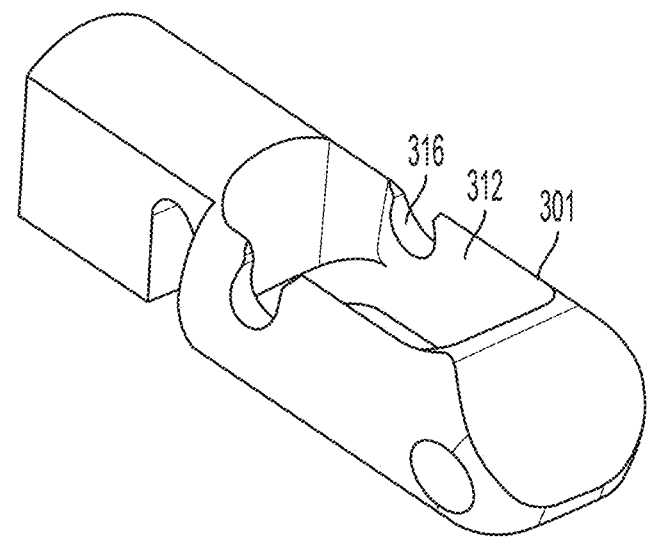
FIGS. 17A-17E are component perspective views of an implant system according to one embodiment, including the body (FIG. 17A), actuator distal end (FIG. 17B), inserter distal end (FIG. 17C), actuator proximal end knob (FIG. 17D), and toggle (FIG. 17E).
Figure 17B:
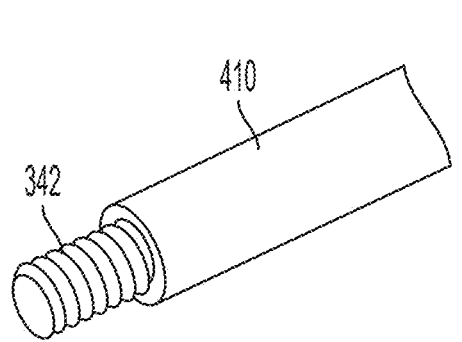
Figure 17C:
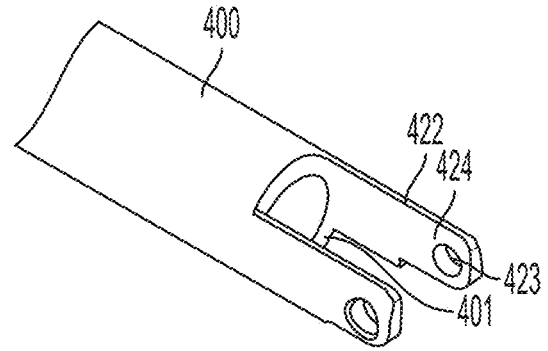
Figure 17D:
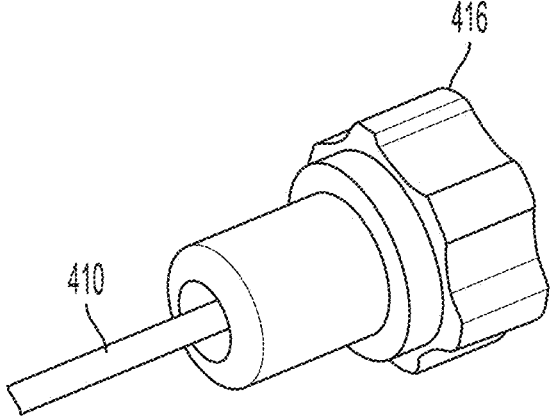
Figure 17E:
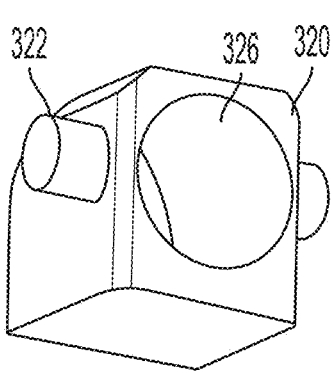
Figure 18B:
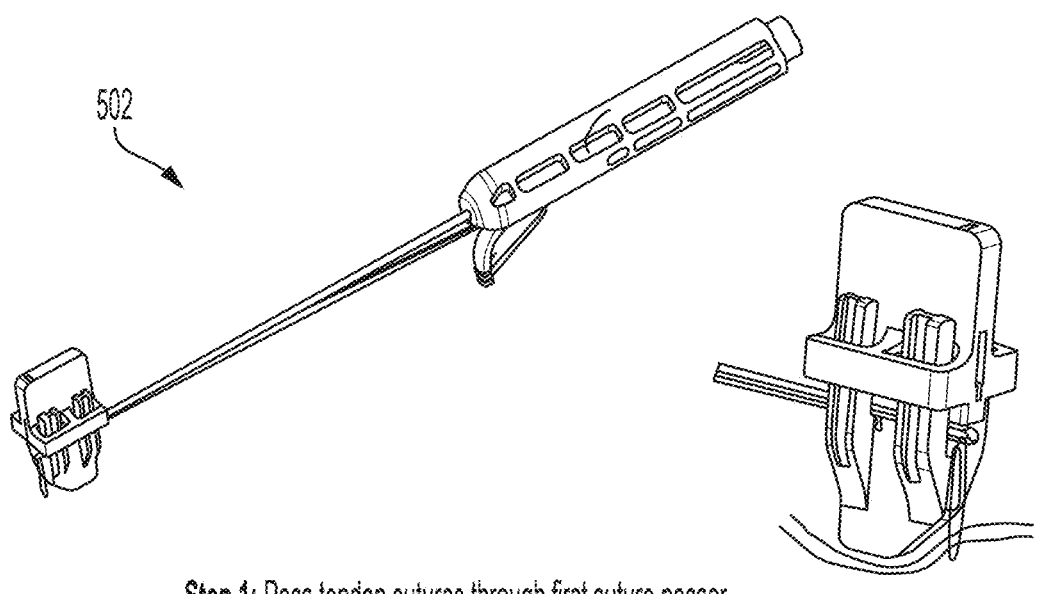
Figure 18C:
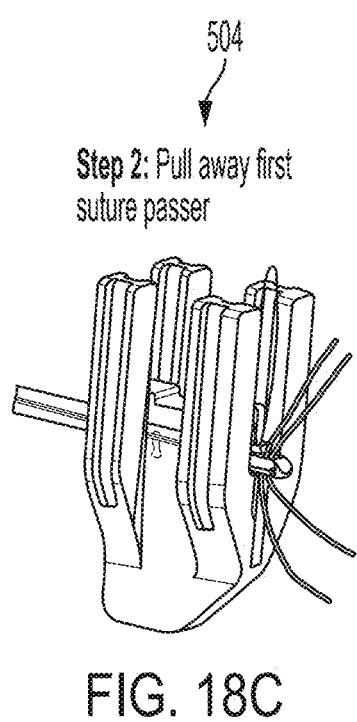
Figure 18D:
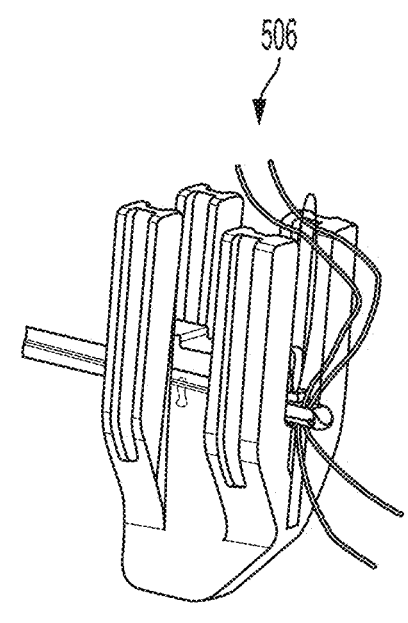
Figure 18E:
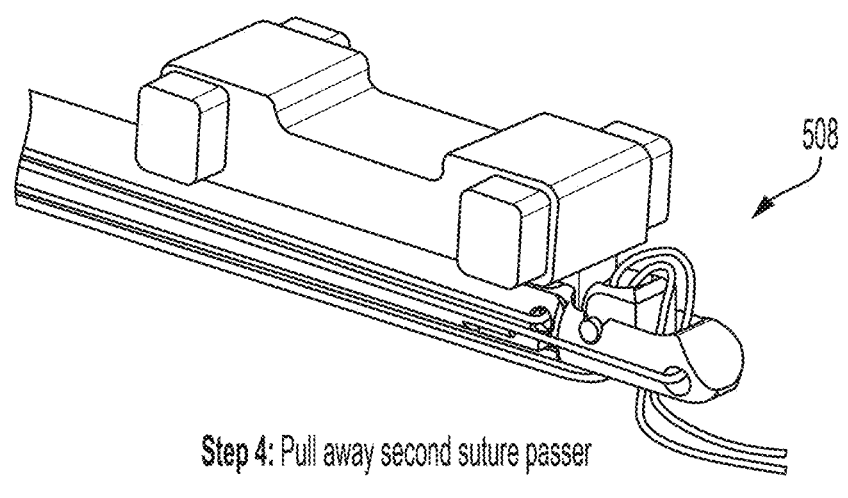
Figure 18F:
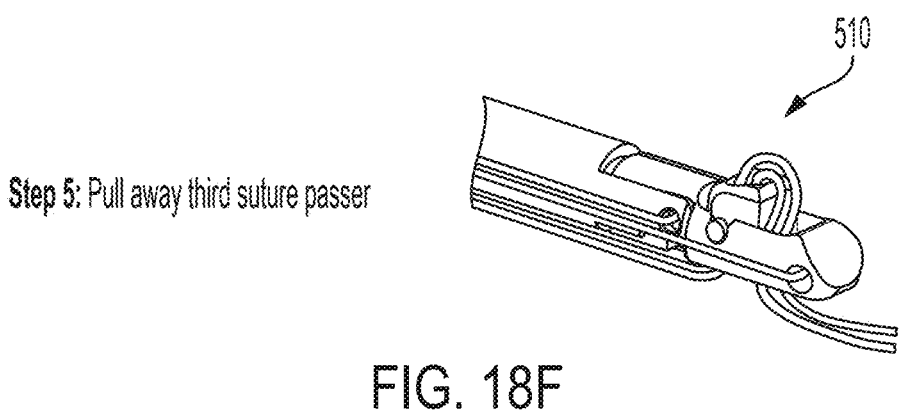
Figure 18G:
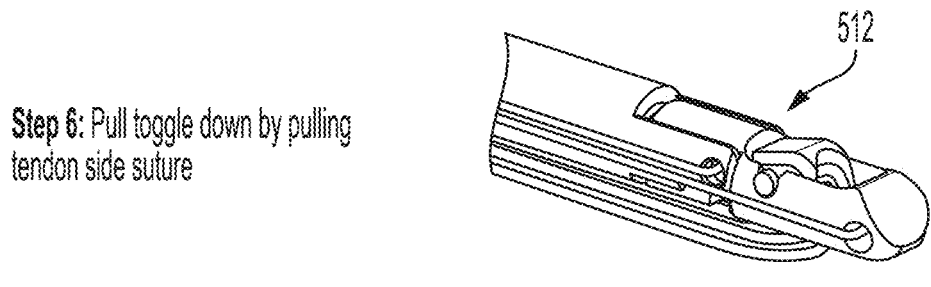
Figure 18H:
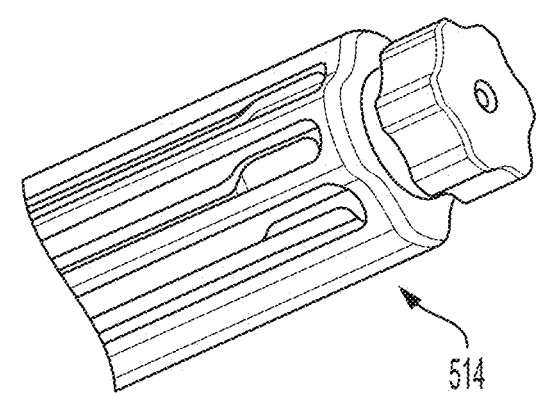
Figure 18I:
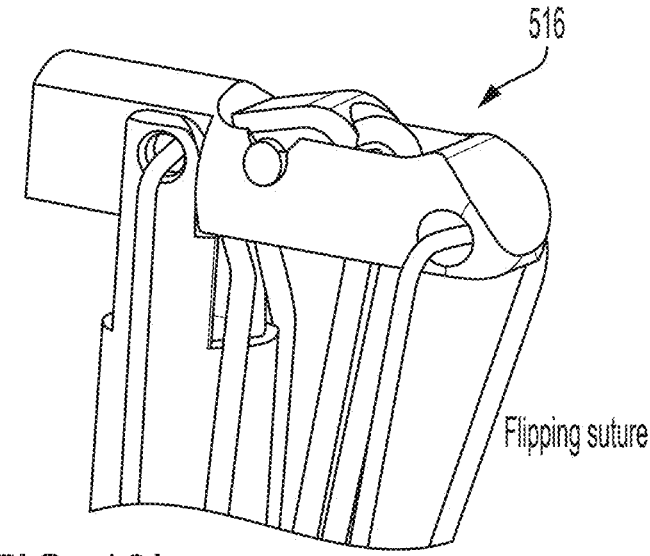
Figure 18J:
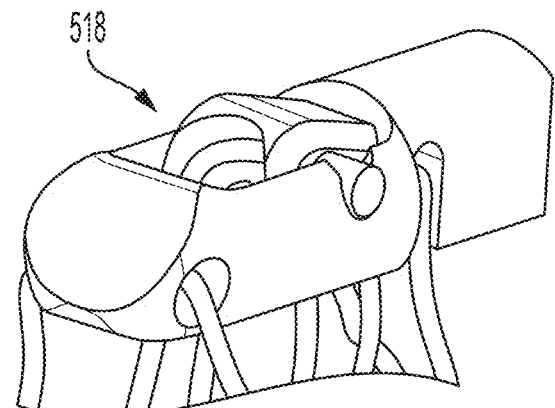
Figures 19A, 19B, 19C, 19D, 19E, 19F:
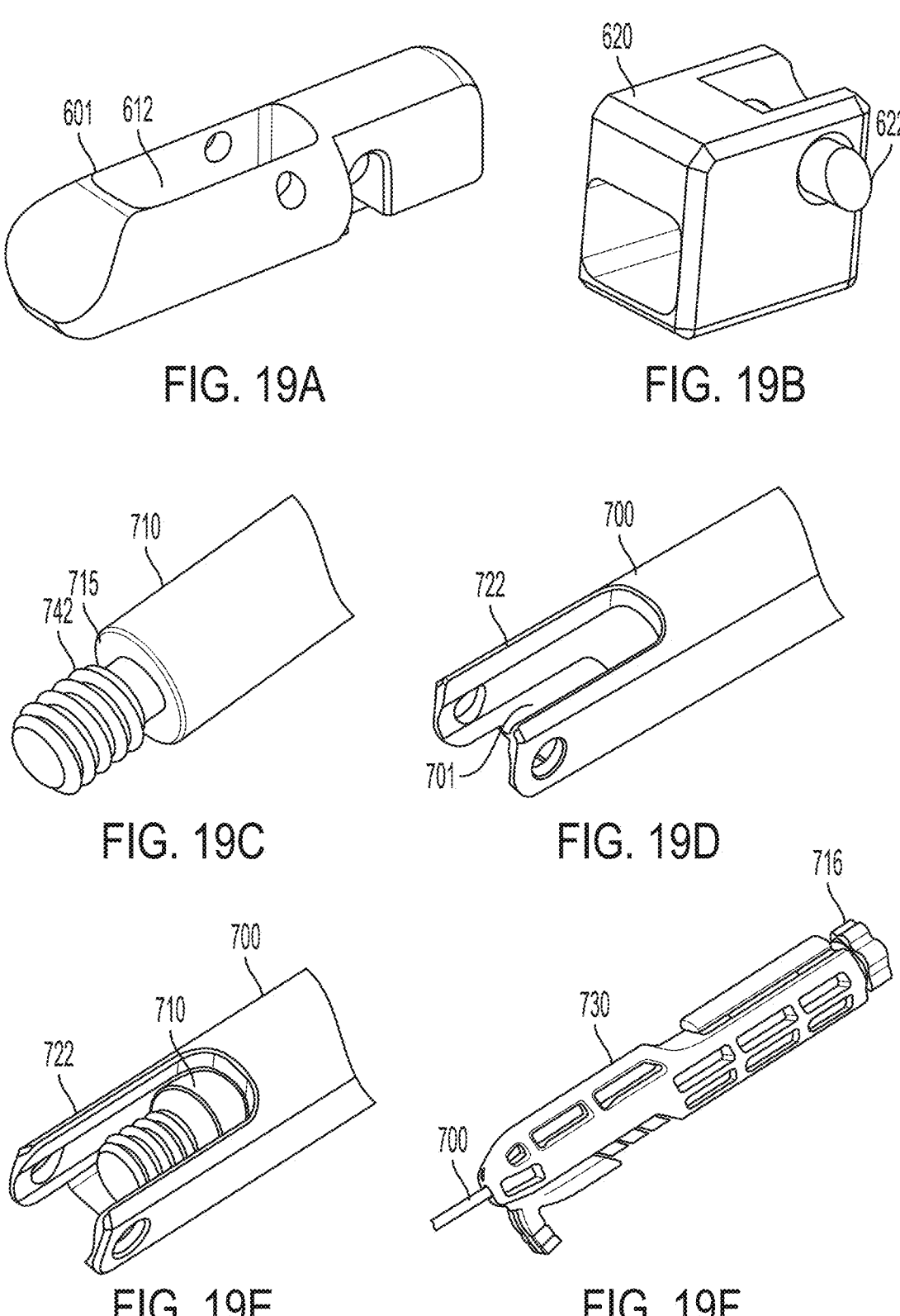
FIGS. 19A-19F are component perspective views of an implant system according to one embodiment, including the body (FIG. 19A), toggle (FIG. 19B), actuator distal end (FIG. 19C), inserter distal end (FIG. 19D), distal end of actuator and inserter assembly (FIG. 19E), and proximal end of actuator and inserter assembly (FIG. 19F).

With reference now to FIGS. 15A and 15B, an embodiment of an implant device 300 according to one embodiment is shown that generally is functionally similar to previous embodiments, however the trunnion component is eliminated and the body 301 instead flips about a pivot suture 330. The implant device 300 has a body 301 having a proximal end 302, a distal end 303, a top side 305 and a bottom side 307. A central cavity 312 is disposed between the proximal end 302 and the distal end 304 for at least partially housing the toggle 320. A proximal opening 314 is disposed proximal to the central cavity 312 to accept insertion of the actuator tip 342, both of which may be threaded to provide a screw-in mating fit. The actuator tip 342 fits into the proximal opening for keeping the body 301 straight when inserted into proximal opening 314 or allowing the body 301 to flip when removed. The central cavity 312 can for example open to the top and bottom of the implant device 300. The geometry of the distal tip 306 of the body 301 is a blunt tip to facilitate advancement through patient anatomy. A set of proximal surfaces 318 can be recessed into the body 301 for interfacing with the inserter as explained in further detail below. The proximal surfaces 318 can be planar or substantially planar. The toggle 320 has a toggle lumen 326 extending therethrough and is at least partially housed within the central cavity 312. The toggle 320 is connected to the body 301 by a toggle hinge connection. The toggle hinge is formed by a set of toggle protrusions 322 disposed on an upper proximal portion of the toggle 320. The body 301 includes a set of toggle hinge openings 316 configured to mate with the set of toggle protrusions 322, collectively forming the toggle hinge connection.

The implant device 300 is used as part of a system including the implant device 300 and an inserter device 400 according to one embodiment. The inserter device 400 has an elongate actuator 410 terminating distally into an actuator tip 342 that can insert into the proximal opening 314 of the body 301. The actuator 410 has a proximal actuator control, which can for example be a twist knob 416. The actuator 410 is movable within a lumen 401 of the inserter device 400, allowing for example a surgeon to rotate the actuator 410 while holding the inserter device 400 stationary.

In one embodiment, a set of distal protrusions or arms 422 are configured to interface with a set of proximal surfaces of the body 301. The interface 424 can be planar or substantially planar to prevent the implant device 300 from turning during actuation. Protrusions at or adjacent to the geometry of this interface 422 permit the body 301 to flip 90 degrees when the actuator 410 is disconnected from the body 301. Other non-planar interface geometries can be implemented to keep the implant device stationary during actuation as will be apparent to those having ordinary skill in the art. The arms 422 each have an arm opening 331 that aligns with an opening 305 in the body 301 to function at a pivot point for flipping the body 301 with the pivot suture is—inserted therethrough.

With reference now to FIGS. 15C-15F, an embodiment of an implant device 300' eliminates the flipping suture, and the body 301' instead flips about a pivot suture 330' by pulling on the tendon sutures only. Similar to previous embodiments, the implant device 300' is used as part of a system including the implant device 300 and an inserter device 400' according to one embodiment. In the various embodiments described herein, since the tendon sutures are disposed distal of the pivot suture 330', the tendon sutures alone are sufficient to flip the body 301'. The geometry of the distal tip 306' of the body 301' remains a blunt tip to facilitate advancement through patient anatomy, and the opening in other embodiments provided for the flipping suture can be eliminated, further smoothing the blunt tip surface profile. A central cavity is disposed between the proximal and distal end 304 for at least partially housing the toggle 320'. Accordingly, method for placing the implant device described herein need not include a separate flipping suture, and may only require the steps of passing a tendon suture through the toggle and the implant device, passing the tendon side of the tendon suture through the implant device and attaching to inserter handle, flipping the toggle down, unscrewing the actuator to allow the implant device to pivot, flipping the implant device, pulling on the inserter device to verify implant device is flipped, and unscrewing the actuator and removing the inserter device.

With reference now to FIGS. 18A-18J, a method 500 for placing an implant device is disclosed according to one embodiment. The method includes the steps of passing tendon sutures though a first suture passer 502, pulling away from the first suture passer 504, passing sutures through the second suture passer 506, pulling away the second suture passer 508, pulling away the third suture passer 510, pulling the toggle down by pulling the tendon side suture 512, inserting the button and then removing the actuator when ready to flip 514, pulling on the sutures passed through the toggle to flip the button 516, and un-cleating the pivot suture and pulling on the inserter 518. As described above, the button can be flipped by the tendon suture alone, and a flipping suture is not required. Alternatively, a separate flipping suture can be utilized and pulled to flip the button. Advantageously, the pivot suture can remain as an additional suture for attachment to soft tissue if desired or removed. In one embodiment, the third suture passer is not required and the procedure of passing the sutures remains the same without the third piece to remove after pulling the second passer away. In one embodiment, the button cannot be released from the inserter unless the button is flipped and the suture axle suture is un-cleated from the handle. Then at this stage, the inserter can be pulled away. This also leaves the suture axle still in the button but removes the inserter.

With reference now to FIGS. 19A-19F, an embodiment of an implant device is shown that generally is functionally similar to previous embodiments, where the body 301 is designed to flip about a pivot suture 330 and the tendon suture is used the flip the button, eliminating any need for a separate flipping suture. Also similar to previous embodiments, the implant device has a body 601 with a central cavity 612 disposed therein, at least partially housing the toggle 620. A proximal opening as in previous embodiments is disposed proximal to the central cavity 612 to accept insertion of the actuator tip 742, both of which may be threaded to provide a screw-in mating fit. The actuator tip 742 fits into the proximal opening for keeping the body 601 straight when inserted into the proximal opening or allowing the body 601 to flip when removed. The actuator stop 715 will tightly interface with the adjacent portion of the body 601, preventing body 601 movement about the hinge connection, locking the implant device 600 at a desired orientation. The geometry of the distal tip of the body 601 is a blunt tip to facilitate advancement through patient anatomy. The inserter device 700 has an elongate actuator 710 terminating distally into an actuator tip 742 that can insert into the proximal opening of the body 700. The actuator 710 has a proximal actuator control, which can for example be a twist knob 716. The actuator 710 is movable within a lumen 701 of the inserter device 700, allowing for example a surgeon to rotate the actuator 710 while holding the inserter device 700 stationary. A set of distal protrusions or arms 722 are configured to interface with a set of proximal surfaces of the body 601. The protrusions at or adjacent to the geometry of this interface 722 permit the body 601 to flip 90 degrees when the actuator 710 is disconnected from the body 601. Other non-planar interface geometries can be implemented to keep the implant device stationary during actuation as will be apparent to those having ordinary skill in the art.

Figure 20A:
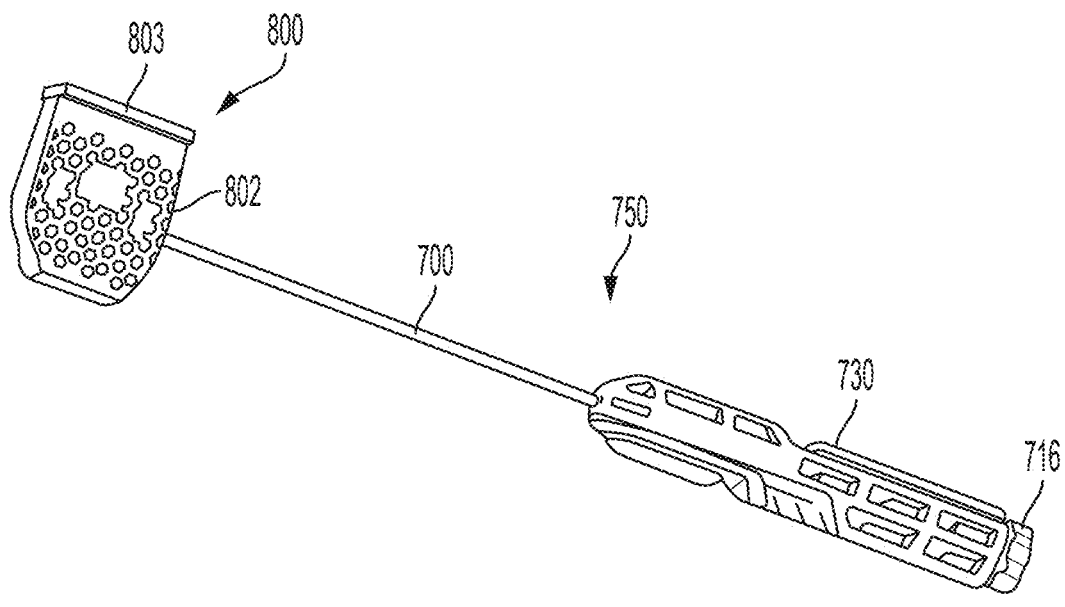
FIG. 20A is a perspective view of an implant system with a suture loading device attached thereto according to one embodiment.
Figure 20B:
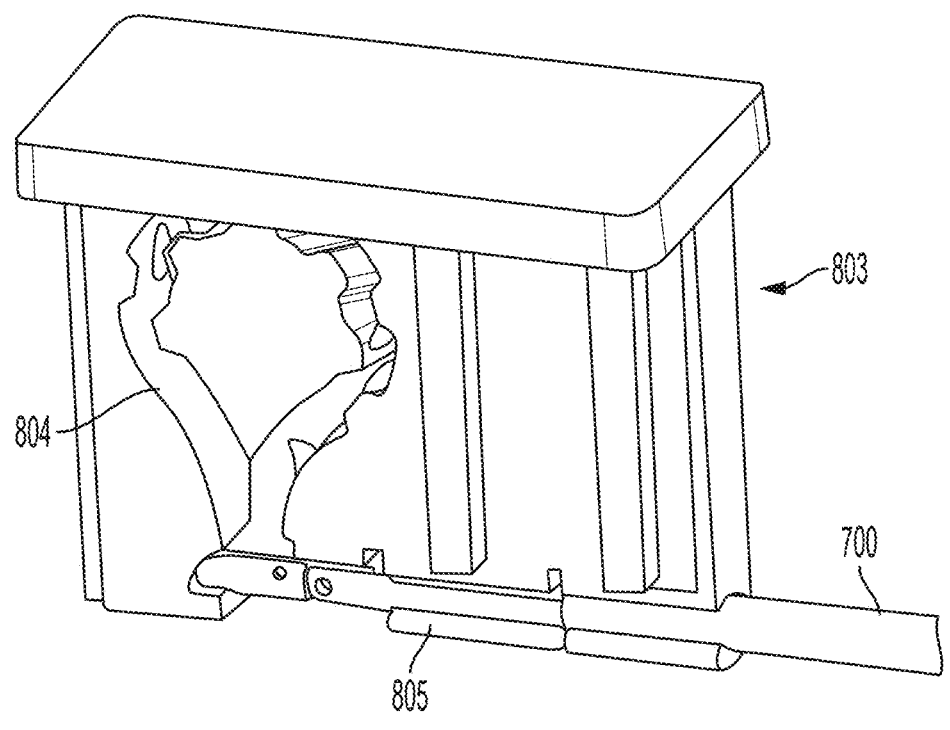
FIG. 20B is a magnified view of the suture loading device with the wire loop tab disconnected according to one embodiment.
Figure 21A:
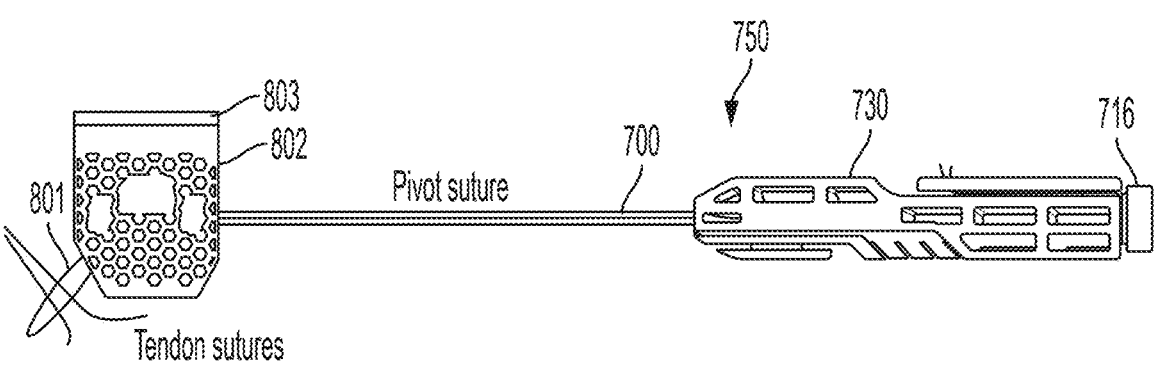
FIGS. 21A-21G are views of loading a suture using the suture loading device followed by steps for unlocking the button to the point of removing the pivot suture according to one embodiment.
Figure 21B:
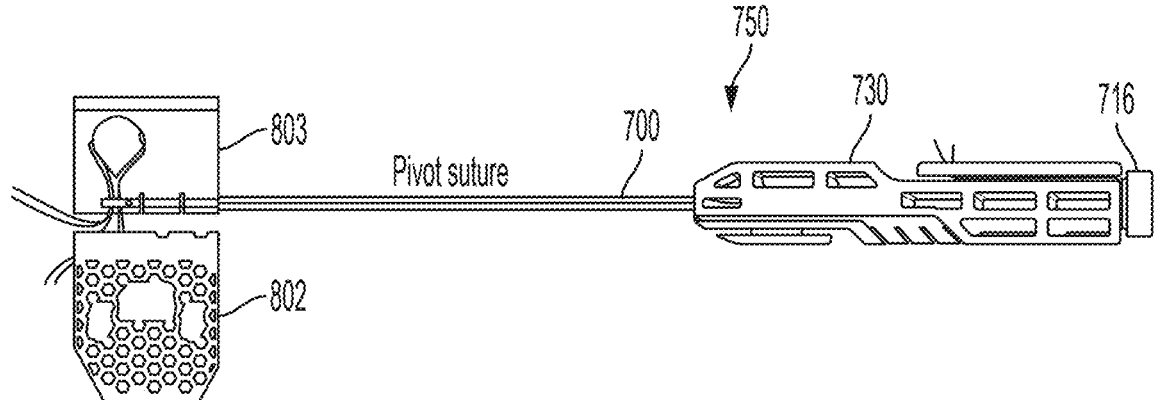
Figure 21C:
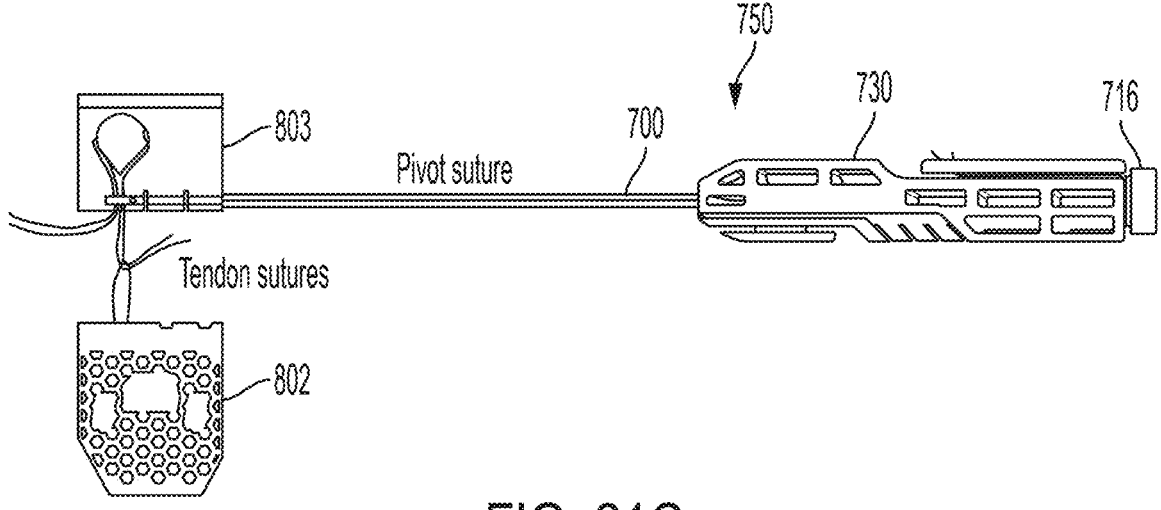
Figures 21D, 21E, 21F, 21G:
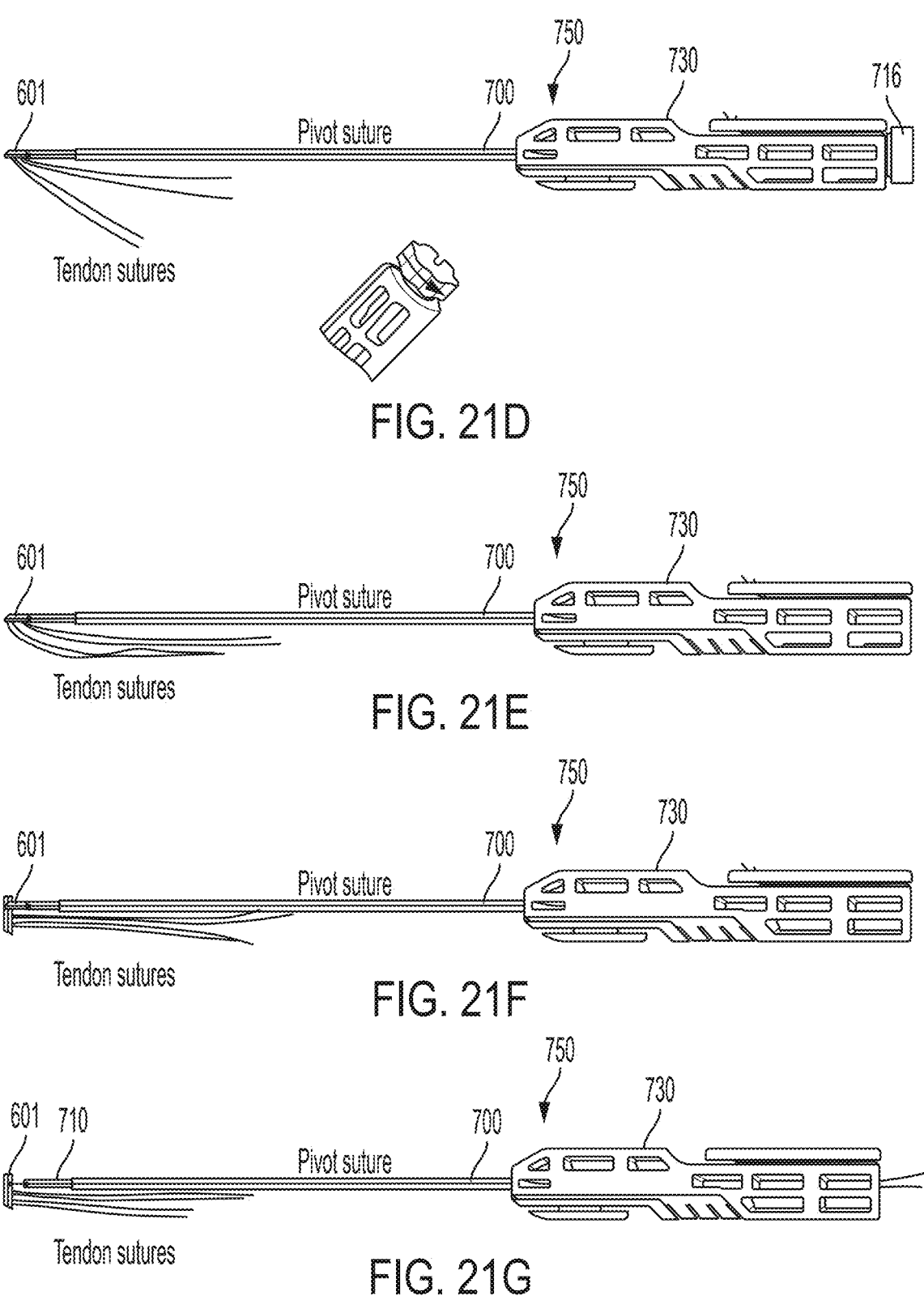

Embodiments of the device in certain instances may not come with a repair suture preloaded. A device and method will now be described for loading a suture through the implant system 750. With reference now to FIGS. 20A and 20B, in one embodiment, an implant system 750 comes preloaded with a suture loading device 800 that assists with passing sutures though the button. The suture loading device includes a wire loop 801 that is preloaded though the button openings and an internal loop path 804 of the suture loading device. First, the sutures are passed though the wire loop 801 (FIG. 21A), which is preloaded though the loading device's internal loop pathway 804. This creates a gradual turn over what is normally a tight turn though the button openings, which for devices like a nitinol wire is a difficult turn to thread. The internal loop pathway 804 creates a more gradual radius, providing a wider turn and low friction pathway for more easily threading the button openings with sutures. The bottom of the internal loop pathway 804 can align with the button openings via a body cavity that creates a snap fit with an outer surface of the inserter device 700, actuator 710, and/or the body 601 of the button. The wire loop tab 802 is pulled down (FIG. 21B), weaving the suture through the button openings via the internal loop path 804 (FIG. 21C). The internal loop tab 803 can then be removed from the implant system 750, as the tendon sutures are now properly threaded for implantation (FIG. 21D). After the actuator is removed (FIG. 21E), the body 601 can be flipped by pulling the tendon sutures (FIG. 21F). The pivot suture can then be unwrapped from the handle 730 and retracted from the body 601 (FIG. 21G). Accordingly, in one embodiment, a suture loading device includes an internal loop tab having an internal loop recessed into a top surface, and a wire loop tab configured to connect to the internal loop tab, wherein the wire loop tab includes a wire loaded within the internal loop. In one embodiment, the wire is configured to pull though the internal loop as the wire loop tab is separated from the internal loop tab. In one embodiment, the wire has a looped portion.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. An implant system comprising: an implant comprising: a body having a proximal end, a distal end, a central cavity disposed between the proximal and distal end, and a proximal end opening disposed proximal to the central cavity, and a toggle at least partially housed within the central cavity and connected to the body by a toggle hinge connection, the toggle having a toggle lumen extending therethrough; and an inserter comprising: an inserter lumen, and an actuator having a distal actuator tip configured to advance into the proximal end opening wherein the inserter comprises a set of distal protrusions configured to interface with a set of proximal surfaces of the body, wherein the interfaces between the set of distal protrusions and the set of proximal surfaces of the body are planar, and wherein an outer surface profile of the system at the interfaces is oval shaped with a flat bottom portion.

2. The implant system of claim 1, wherein both the distal actuator tip and the proximal end opening are threaded.

3. The implant system of claim 1, wherein a proximal end of the actuator comprises a knob.

4. The implant system of claim 1, wherein a distal end of the inserter comprises at least one arm.

5. The implant system of claim 4, wherein the at least one arm comprises a first opening.

6. The implant system of claim 5, wherein the at least one arm is a first arm and a second arm and wherein the first arm comprises the first opening and the second arm comprises a second opening, wherein the first opening and the second opening align with a pivot suture opening in the body.

7. The implant system of claim 1, wherein the body is restricted to flipping between an insertion position and a 90-degree flipped position.

8. The implant system of claim 1, wherein a proximal portion of the body is configured with a geometry accommodating a plurality of locked orientation angles.

9. The implant system of claim 1, wherein the toggle is configured to exert a unidirectional locking force.

10. The implant system of claim 9, wherein the unidirectional locking force corresponds to a distance between the toggle and an adjacent wall of the body that can vary based on suture size.

11. The implant system of claim 10, wherein the distance decreases as the toggle closes.

12. The implant system of claim 10, wherein an angle between the toggle and the adjacent wall of the body changes as the toggle closes.

13. The implant system of claim 10, wherein the toggle is configured to exert the unidirectional locking force at a plurality of distances from the adjacent wall of the body.

14. The implant system of claim 1, wherein the body comprises a distal tip lumen extending laterally through the body.

15. The implant system of claim 1, wherein the distal end of the body has a blunt tip.

16. The implant system of claim 1, wherein the toggle hinge connection comprises a set of toggle protrusions disposed on an upper proximal portion of the toggle.

17. The implant system of claim 16, wherein the body comprises a set of toggle hinge openings configured to mate with the set of toggle protrusions.

18. The implant system of claim 1, wherein the set of proximal surfaces of the body are recessed into the body.

19. The implant system of claim 1, wherein an outer surface profile of the implant system at the toggle is oval shaped with a flat bottom portion.

20. The implant system of claim 1, wherein an outer surface profile on the implant system at the interfaces and the toggle is the same profile.

21. The implant system of claim 1, wherein the actuator extends through a proximal opening in an inserter handle.

22. The implant system of claim 21, wherein a proximal actuator control is connected to the actuator proximal of the inserter handle.

23. The implant system of claim 22, wherein the proximal actuator control is a twist knob.

24. The implant system of claim 21, wherein the inserter handle comprises a curved arm extending away from a proximal end of the inserter handle.

25. The implant system of claim 24, wherein the curved arm is flexible.

26. The implant system of claim 24, wherein the inserter handle comprises a channel adjacent to the curved arm.

27. A kit comprising the implant system of claim 1 and a suture preloaded through a distal tip lumen extending laterally through the body.

28. A kit comprising the implant system of claim 1 and a preloaded pivot suture.

29. A method for placing an implant device, the method comprising: providing the implant system of claim 1; passing a tendon suture through the toggle and the implant device; passing the tendon side of the tendon suture through the implant device and attaching to inserter handle; flipping the toggle down; unscrewing the actuator to allow the implant device to pivot; flipping the implant device; pulling on the inserter device to verify implant device is flipped; and unscrewing the actuator and removing the inserter device.

30. A biceps tenodesis surgical procedure comprising a method for placing an implant device, the method comprising: providing the implant system of claim 1; passing a tendon suture through the toggle and the implant device; passing the tendon side of the tendon suture through the implant device and attaching to inserter handle; flipping the toggle down; unscrewing the actuator to allow the implant device to pivot; flipping the implant device; pulling on the inserter device to verify implant device is flipped; and unscrewing the actuator and removing the inserter device.

31. A shoulder, elbow, hand, wrist, knee, foot, ankle or hip surgical procedure comprising a method for placing an implant device, the method comprising:

providing the implant system of claim 1; passing a tendon suture through the toggle and the implant device; passing the tendon side of the tendon suture through the implant device and attaching to inserter handle; flipping the toggle down; unscrewing the actuator to allow the implant device to pivot; flipping the implant device; pulling on the inserter device to verify implant device is flipped; and unscrewing the actuator and removing the inserter device.

* * * * *